United States Patent [19]

Sherwin

[11] Patent Number: 5,052,401
[45] Date of Patent: Oct. 1, 1991

[54] PRODUCT DETECTOR FOR A STEADY VISUAL EVOKED POTENTIAL STIMULATOR AND PRODUCT DETECTOR

[75] Inventor: Gary W. Sherwin, Yukon, Pa.

[73] Assignee: Westinghouse Electric Corp., Pittsburgh, Pa.

[21] Appl. No.: 327,047

[22] Filed: Mar. 22, 1989

Related U.S. Application Data

[62] Division of Ser. No. 893,758, Aug. 6, 1986, Pat. No. 4,861,154.

[51] Int. Cl.$^5$ .............................................. A61B 5/04
[52] U.S. Cl. .................................. 128/745; 329/358; 128/731
[58] Field of Search ...................... 128/731, 745, 746; 310/110, 122, 125; 329/122, 124

[56] References Cited

U.S. PATENT DOCUMENTS 3,951,134  4/1976  Malech ........................... 128/731 X
4,697,598  10/1987  Bernard et al. ..................... 128/731

Primary Examiner—Francis Jaworski
Attorney, Agent, or Firm—John K. Williamson

[57] ABSTRACT

An automated visual testing system is disclosed which presents an alternating steady state visual stimulus to a patient through an optical system that modifies the stimulus image. As the image changes, the patient produces evoked potentials that change. The evoked potentials are detected by a product detector which produces the amplitude of the evoked potentials. The product detector includes filters which isolate the patient's evoked potentials, a modulator which detects the response using the stimulus source frequency and a demodulator that determines the amplitude of the response. The product detector detects the level of the steady state evoked potential signals even in the presence of substantial background noise and extraneous electroencephalograhic signals. These detectors can be used to monitor the evoked potential produced by visual, aural or somatic steady state stimuli. The components described above can be used to produce a system that can determine to which of several different displays an observer is paying attention by providing images that blink at different frequencies and product detectors for each of the stimulus frequencies. The product detector producing the highest output indicates the display upon which the observer is focused.

1 Claim, 37 Drawing Sheets

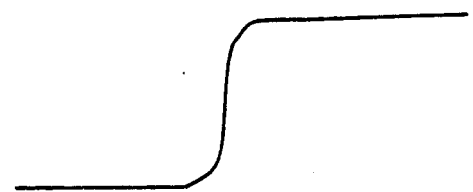
FIG. 12.    CONTRAST
AMPLITUDE
OF
RESPONSE
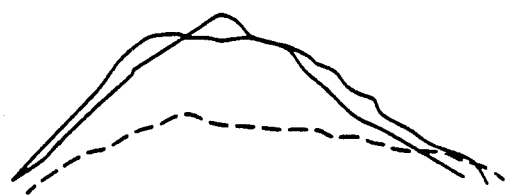
FIG. 13.    SPATIAL FREQUENCY
THRESHOLD
FIG. 14.    COLOR INTENSITY
AMPLITUDE
OF
RESPONSE
NORMAL
COLOR DEFICIENT

FIG. 15B1.

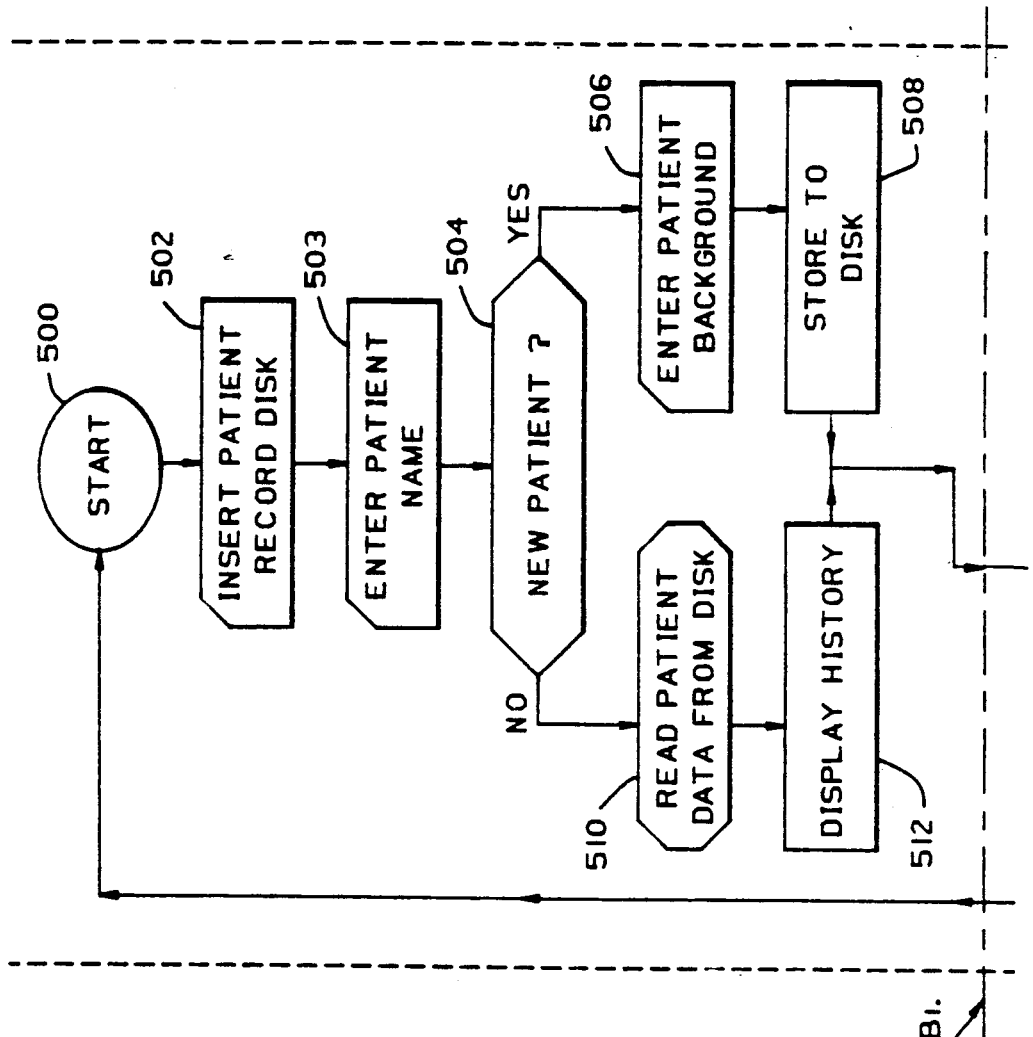
FIG. 15B2.

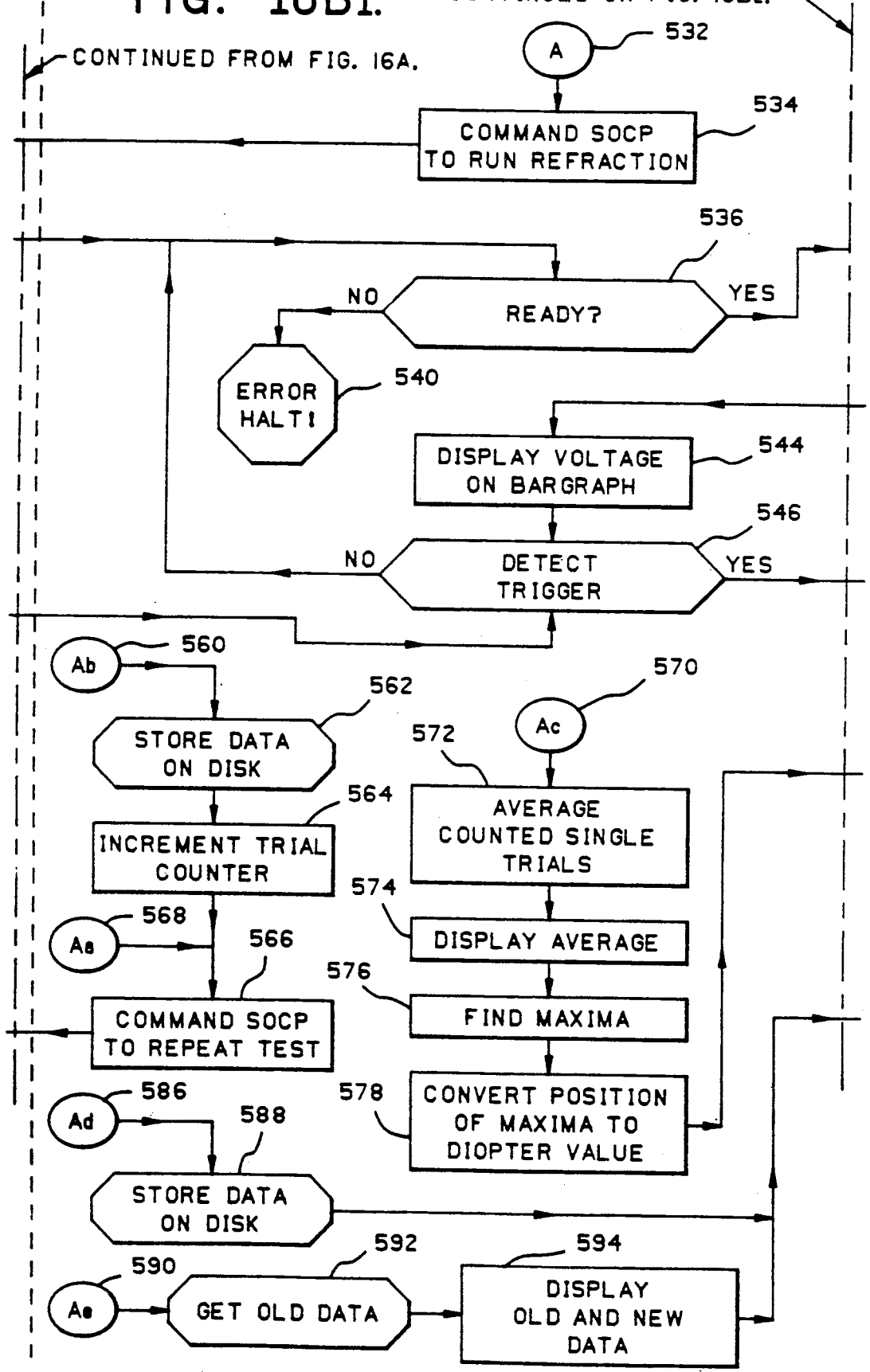
FIG. 16B1.

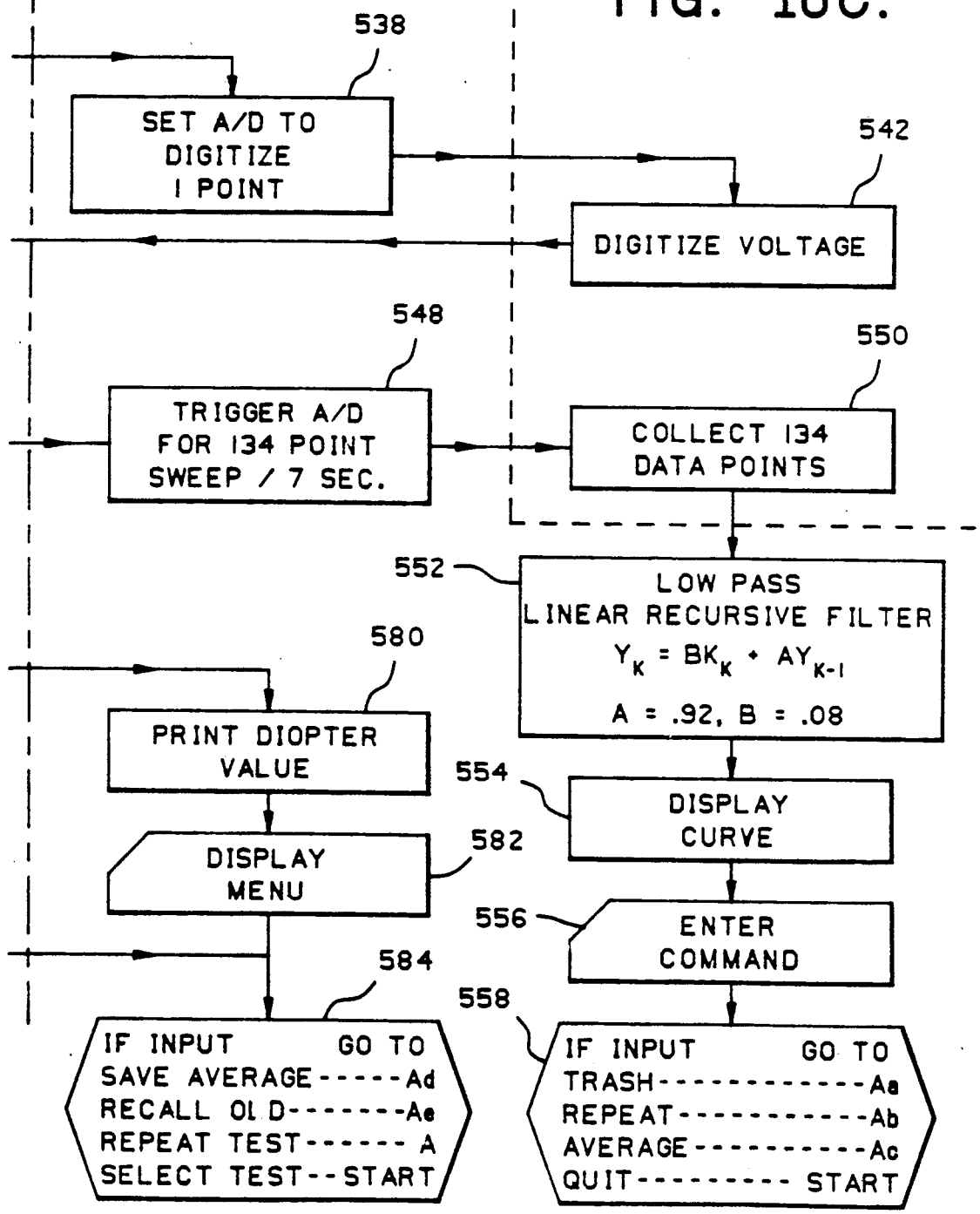

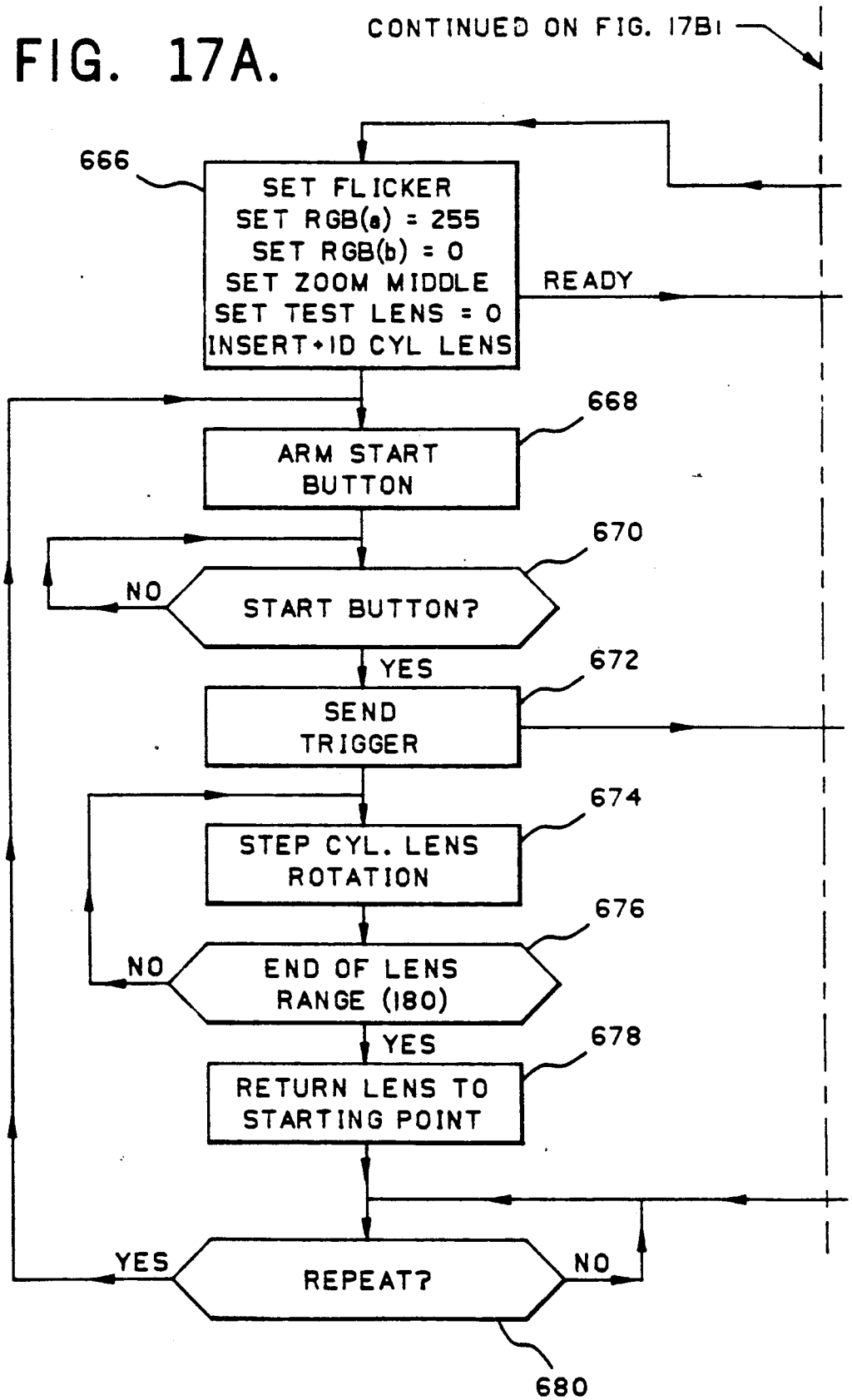

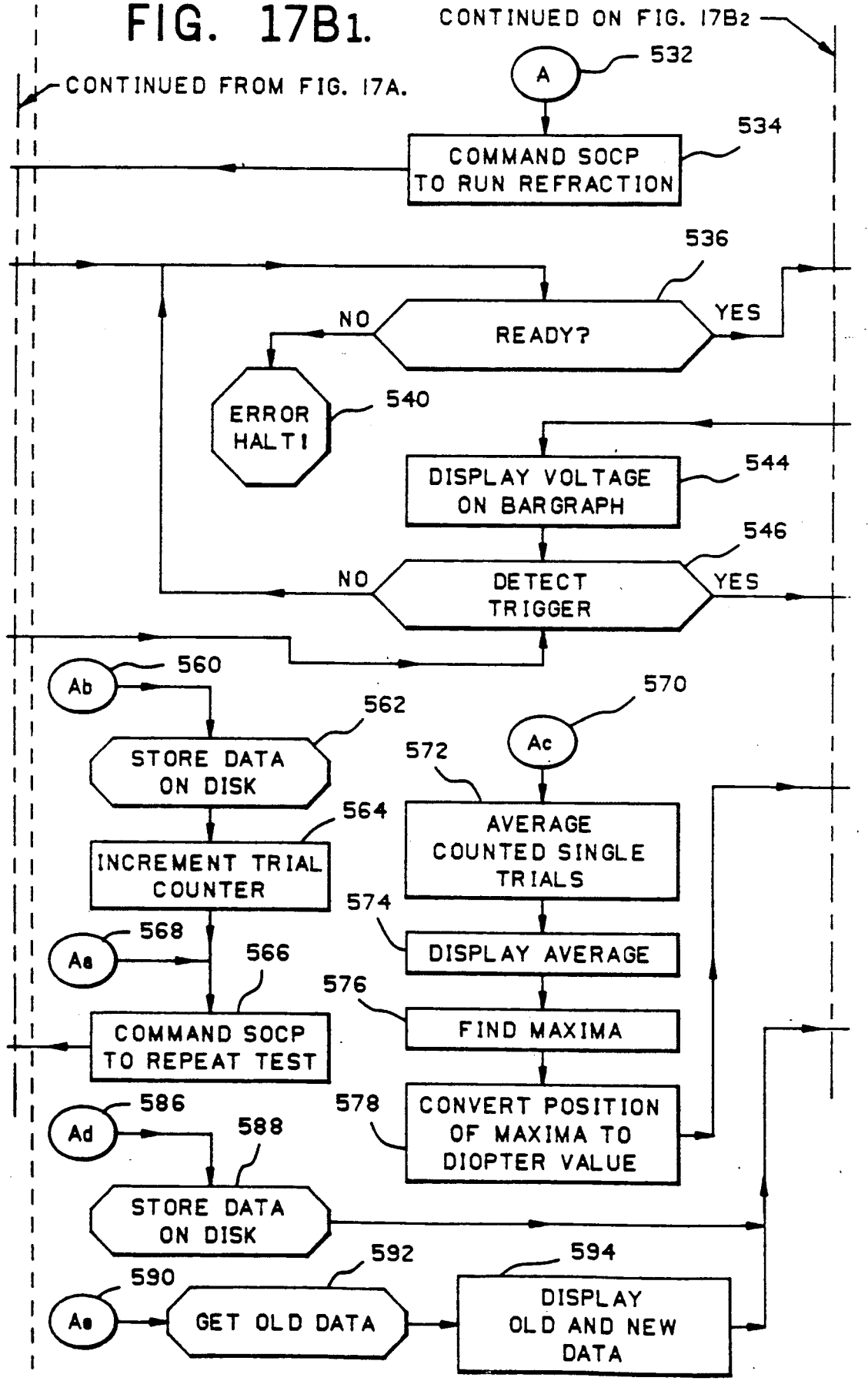

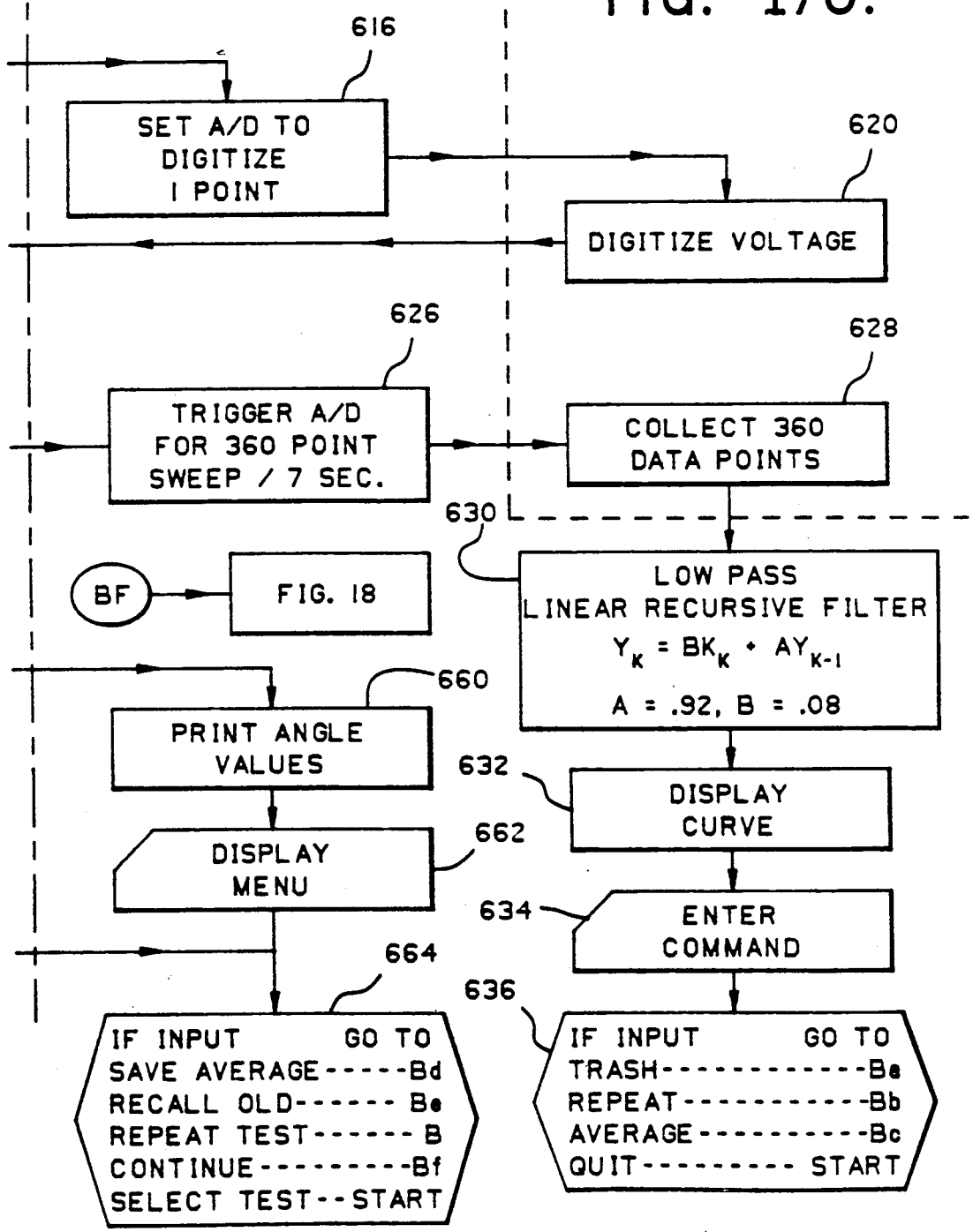

FIG. 18B1.
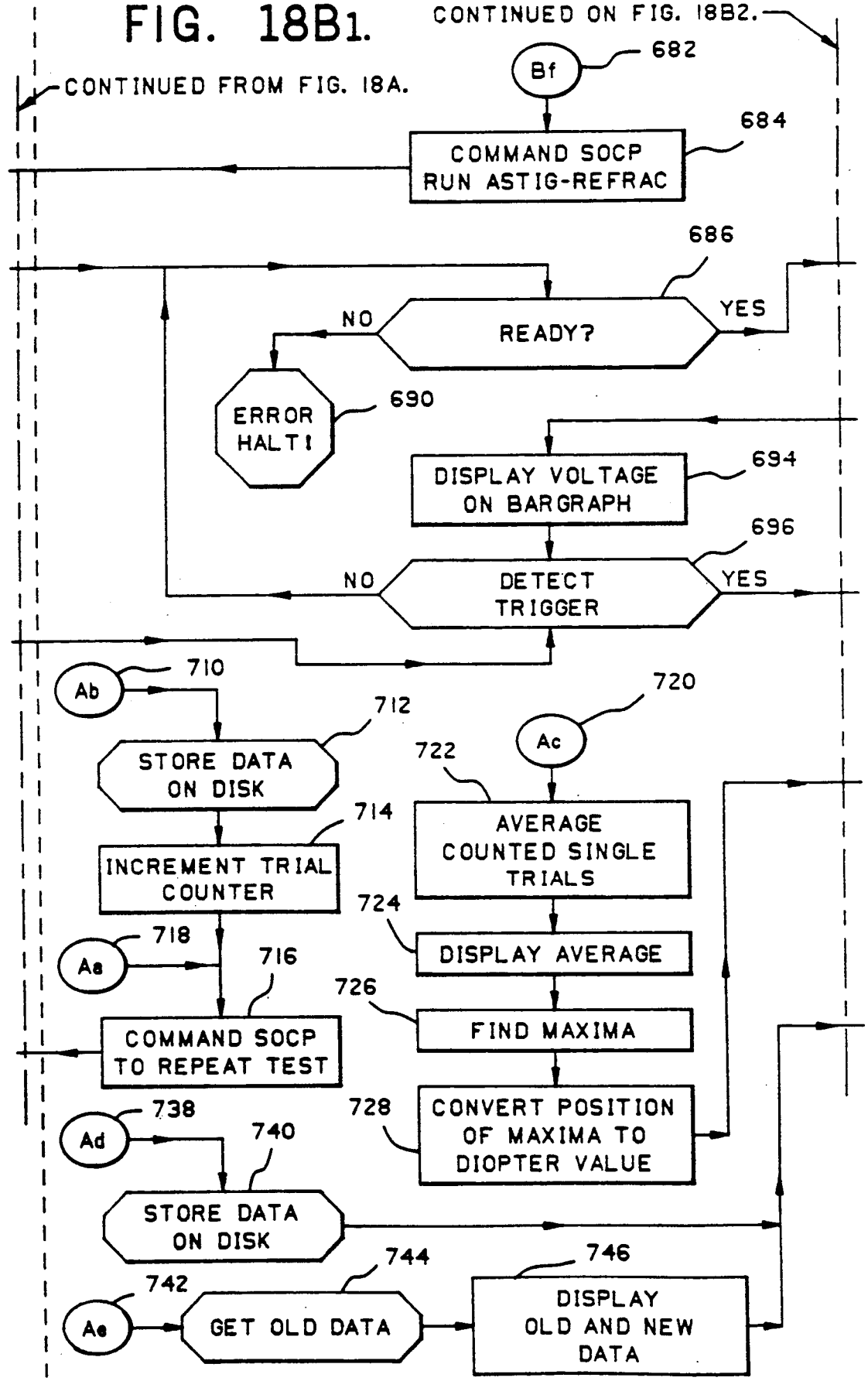

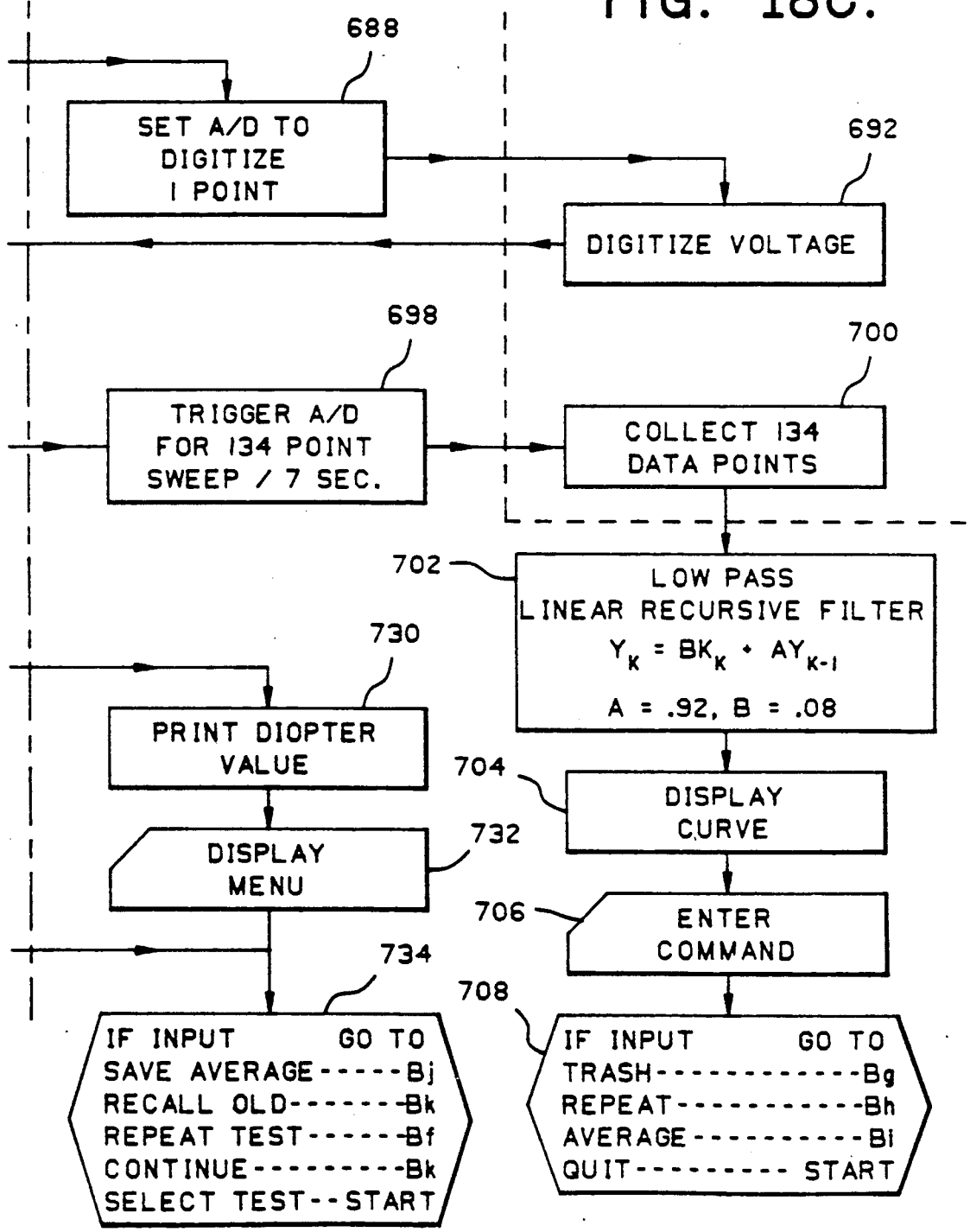

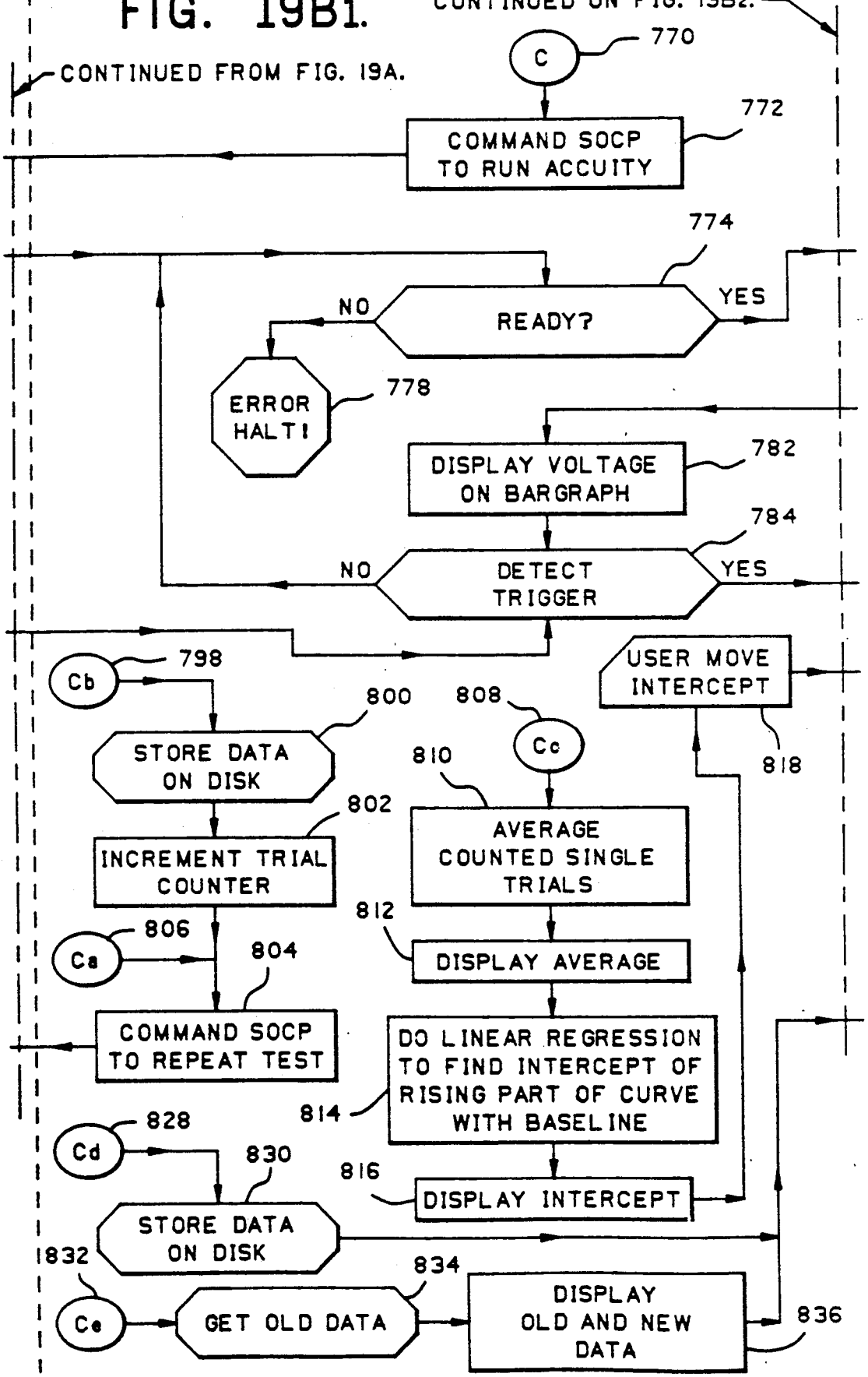

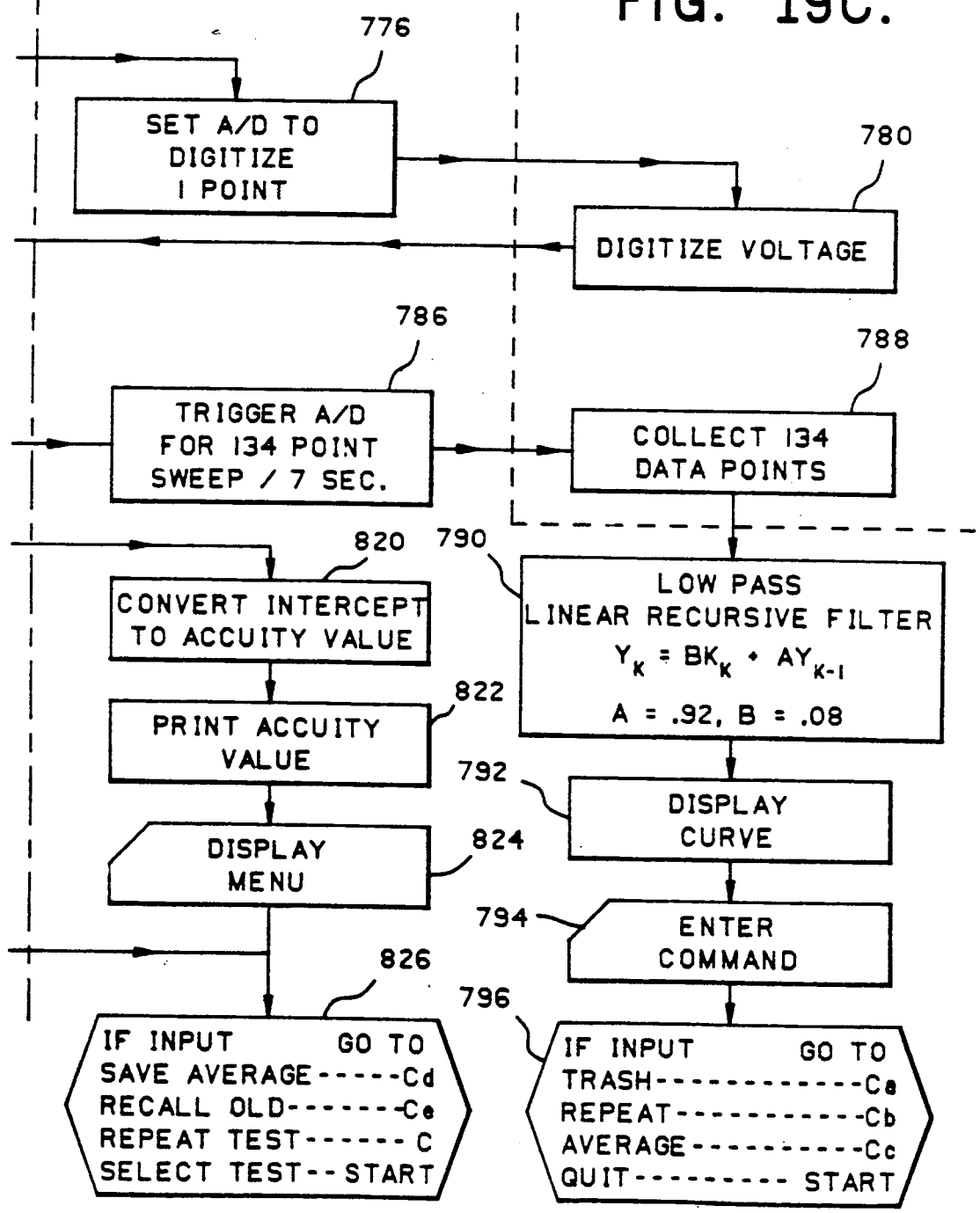

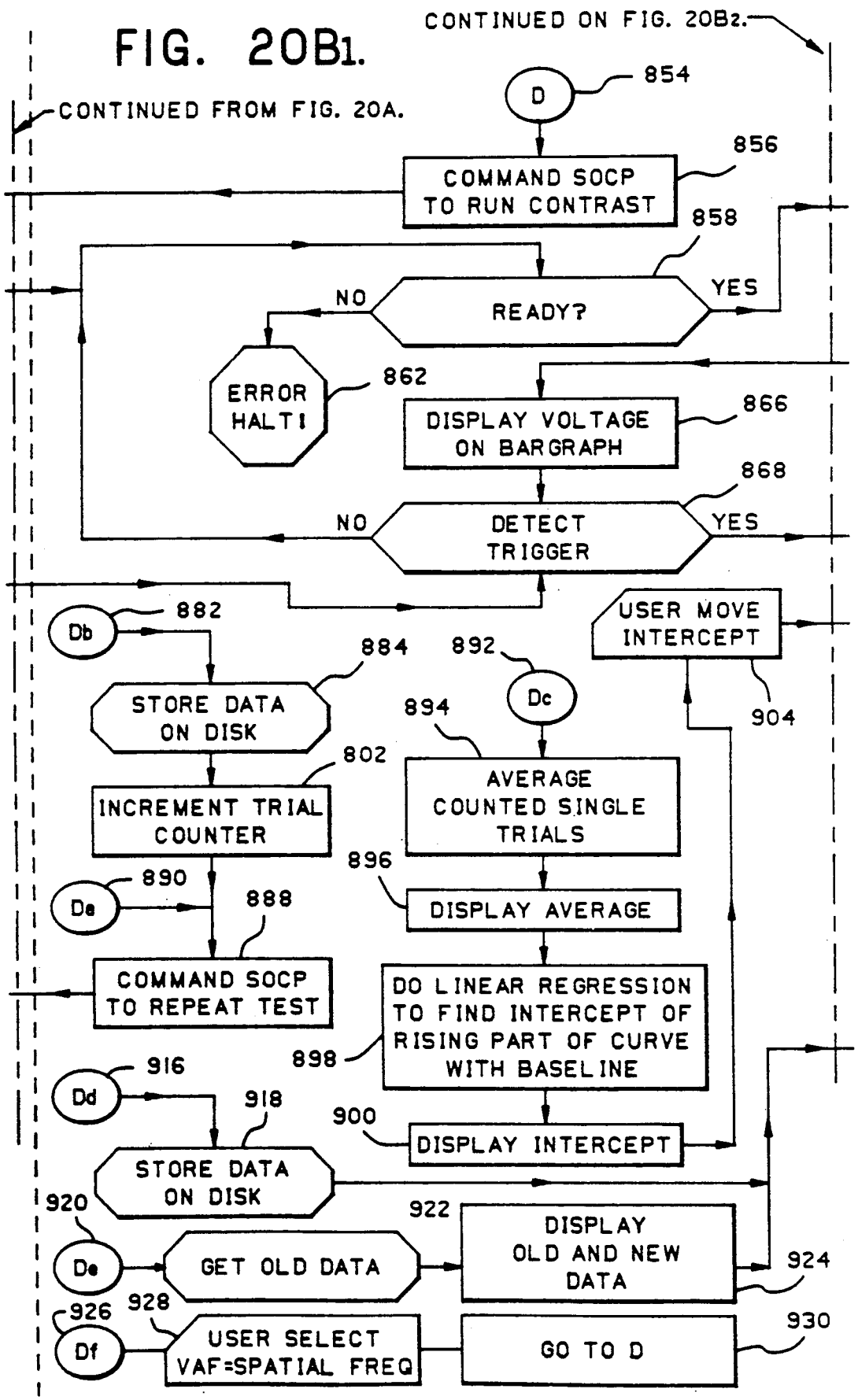
FIG. 20B1.

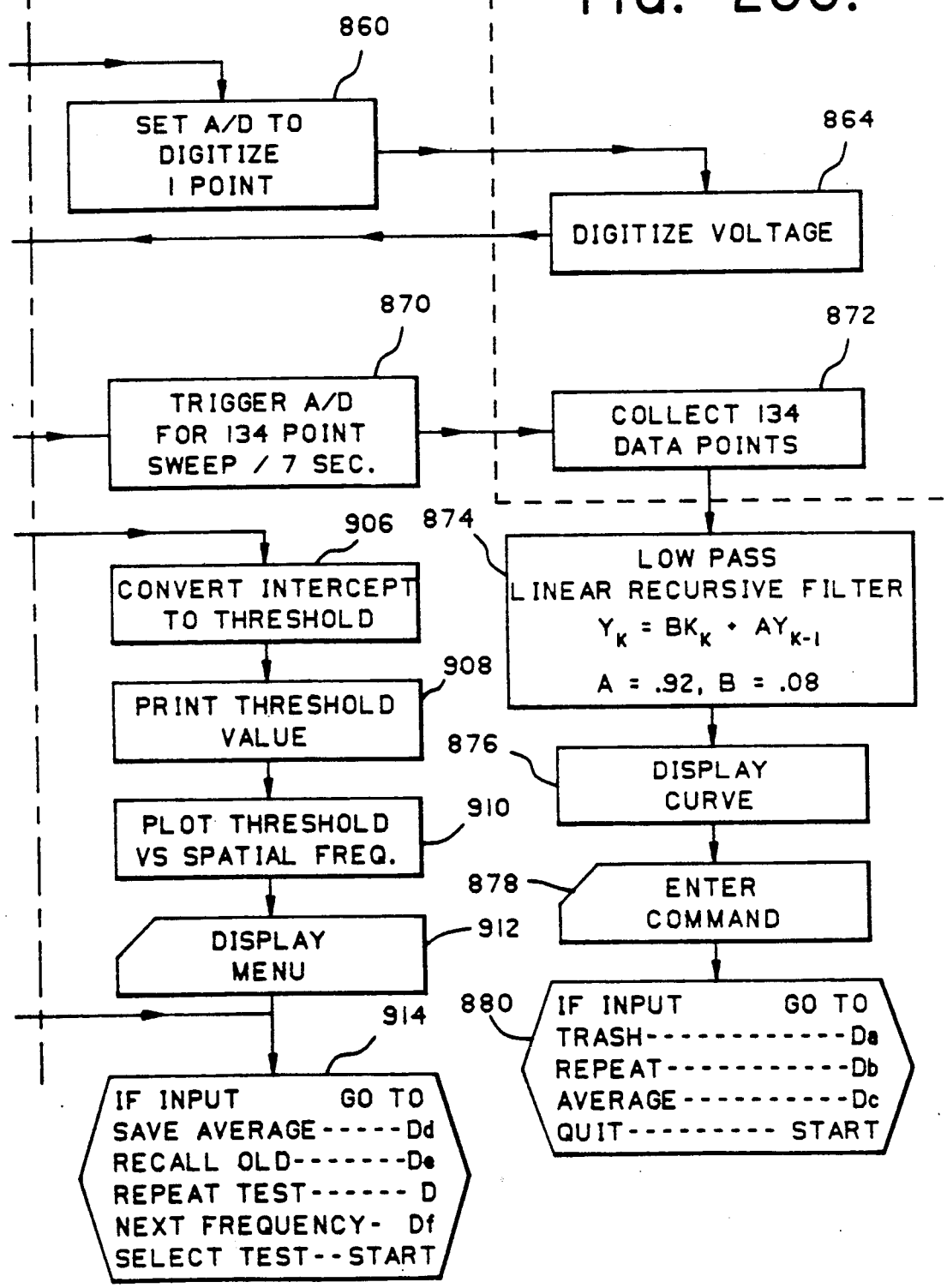

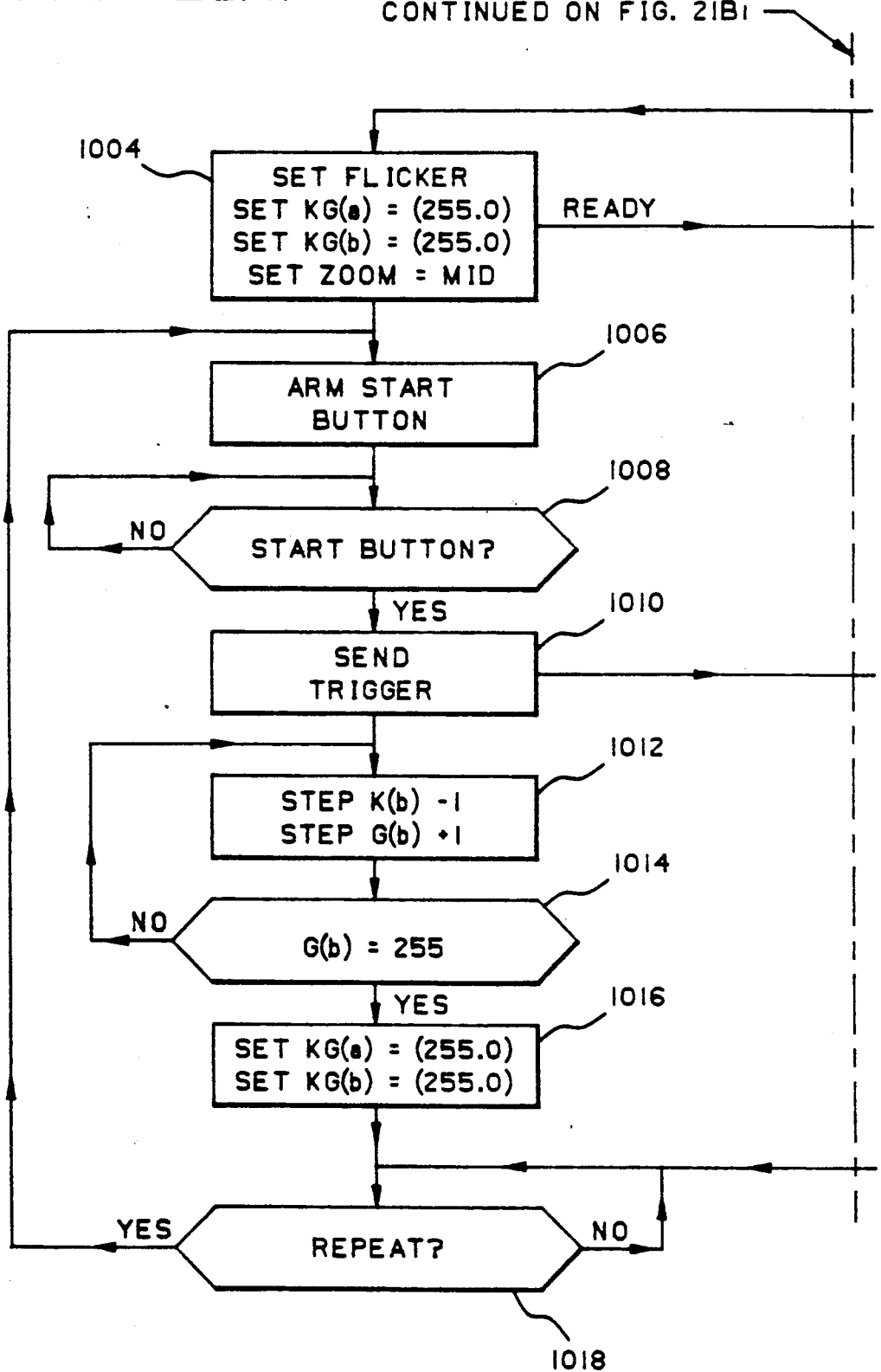

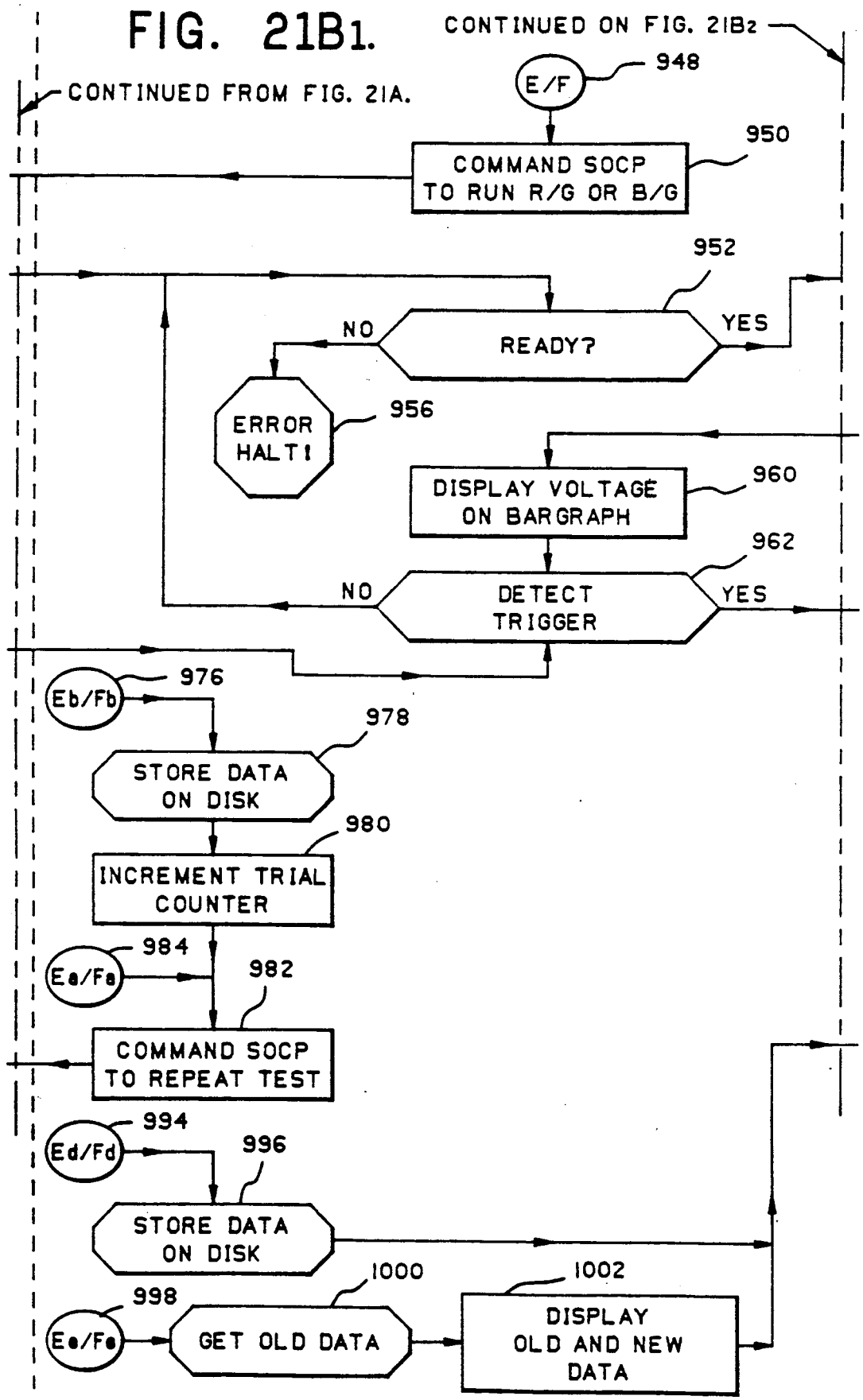

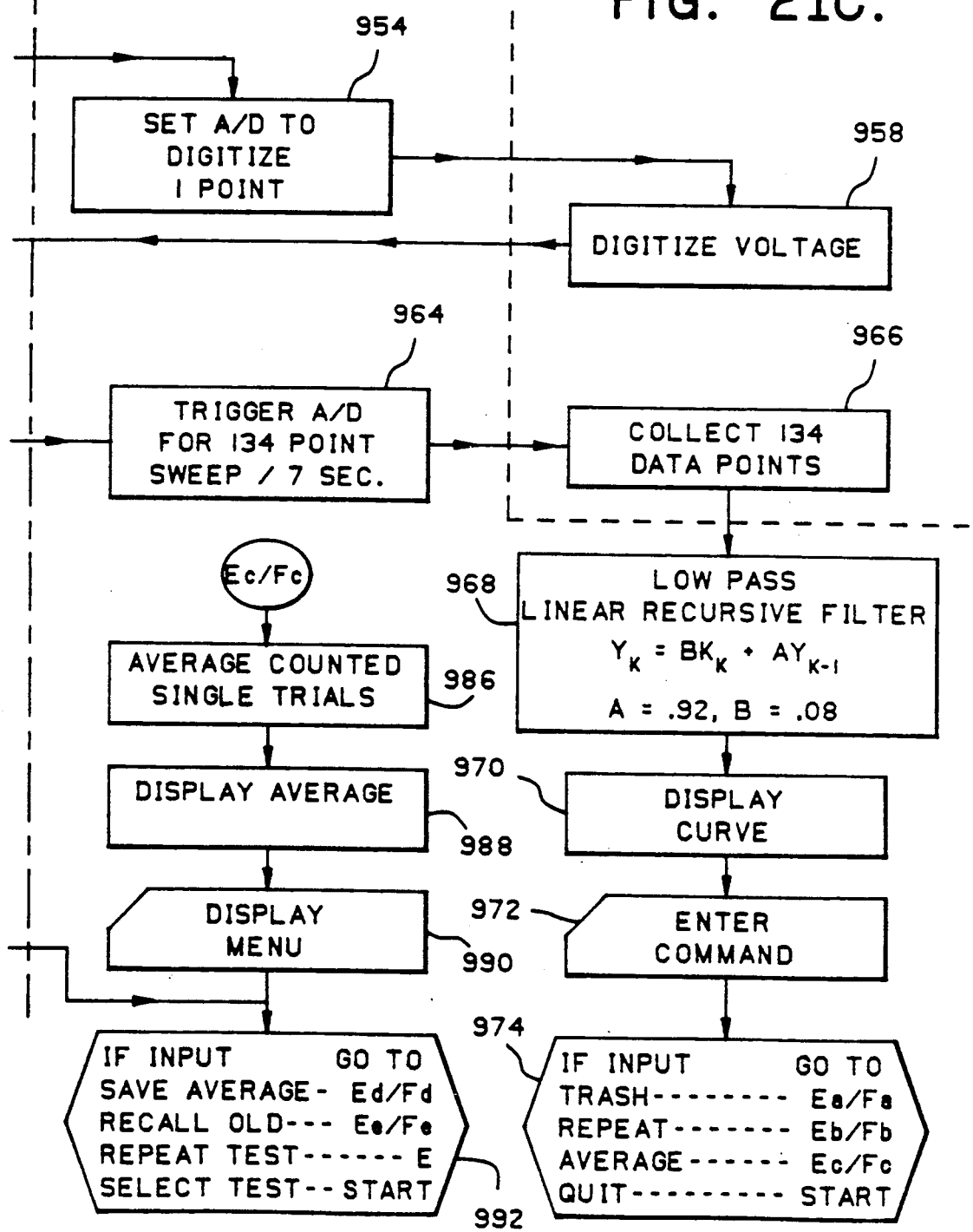

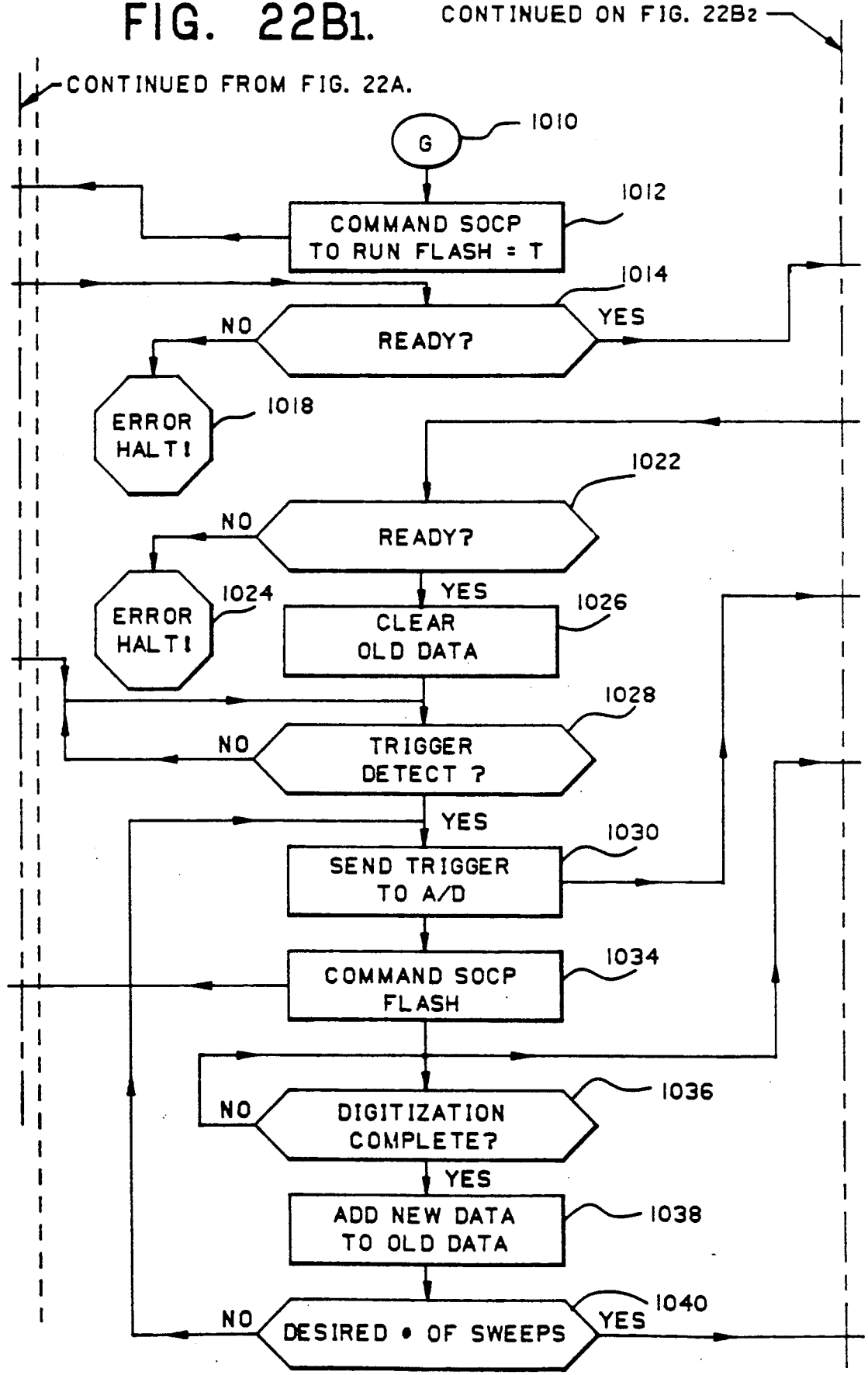
FIG. 22B1.

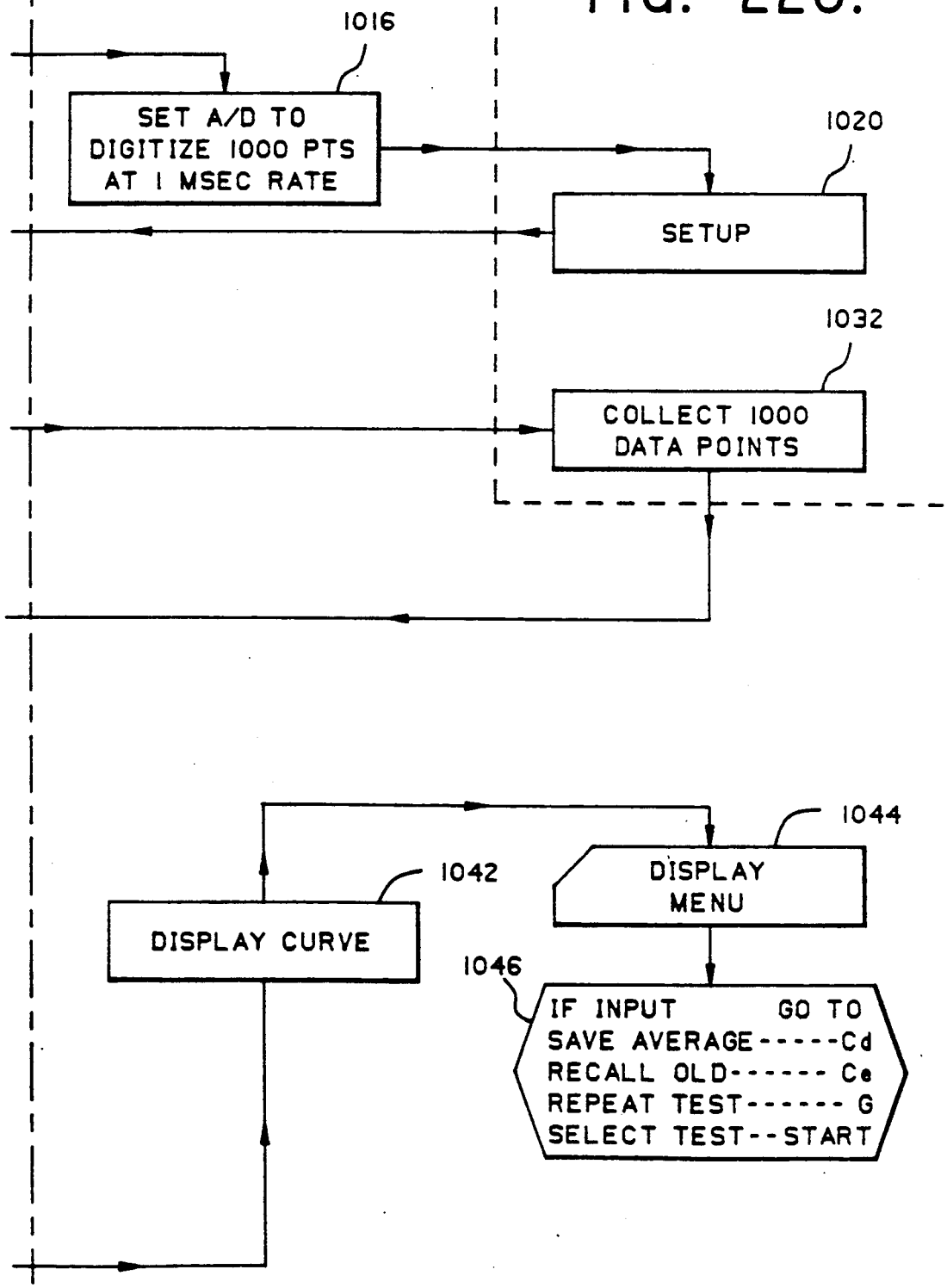

PRODUCT DETECTOR FOR A STEADY VISUAL EVOKED POTENTIAL STIMULATOR AND PRODUCT DETECTOR

CROSS REFERENCES TO RELATED APPLICATIONS

This application is a Divisional application of U.S. Ser. No. 893,758 filed Aug. 6, 1986, and now U.S. Pat. No. 4,861,154.

This application is related to the following co-pending U.S. applications assigned to the assignee of the present invention: An Electroencephalographic Headset with a Disposable Monitor and Disposable Electrolyte Applicator by Sherwin et al. having U.S. Ser. No. 822,725 now U.S. Pat. No. 4,706,679; Low Noise EEG Probe Wiring System by Sherwin et al. having U.S. Ser. No. 727,060 now U.S. Pat. No. 4,678,865; Narrow Band EEG Amplifier by Sherwin et al. having U.S. Ser. No. 727,056 now U.S. Pat. No. 4,679,002; Evoked Potential Autorefractometry System by Bernard et al. having U.S. Ser. No. 727,032 now U.S. Pat. No. 4,679,598; and concurrently-filed U.S. patent application entitled A Precision Patterned Mirror and Method of Making Same by Sherwin et al. and having U.S. application Ser. No. 893,759 filed Aug. 6, 1986, now abandoned. The above-mentioned co-pending U.S. patent applications are incorporated by reference herein.

BACKGROUND OF THE INVENTION

1. Field of the Invention

The present invention relates to an automated visual assessment system suitable for performing a variety of vision tests and, more particularly, to an evoked potential vision testing system which performs spherical and aspherical refractometry, contrast sensitivity, color sensitivity, acuity, transient pattern and flash evoked potential tests for visual pathway disfunction which is low in cost, does not intimidate a patient and provides a highly accurate easy-to-use vision testing system.

2. Description of the Related Art

Typical vision testing systems in an eye doctor's office include a plurality of separate testing systems which each provide a different test. These individual tests take at least 10 minutes each, resulting in at least an hour in a doctor's office for a comprehensive vision test. For example, eye refraction is generally measured by placing lenses of different refractive power in front of the patient's eye and allowing the patient to indicate whether or not the visual target has improved in focus, a process that can take up to 30 minutes, while color vision testing is typically performed using flash cards having images of different colors which the patient is asked to detect. These vision testing systems, even though each is a separate device all have a single common feature, all require that the patient verbally cooperate to indicate the results of the tests.

SUMMARY OF THE INVENTION

It is an object of the present invention to provide an automated visual assessment system suitable for a commercial environment.

It is a further object of the present invention to provide a frequency locked evoked potential detector capable of detecting the brain wave patterns produced by a patient when viewing a steady state evoked potential stimulator.

It is an object of the present invention to provide a detector capable of detecting steady state evoked potentials produced in the human brain when caused by visual, aural or somatic steady state stimuli.

It is also an object of the present invention to provide a product detector that is capable of changing the detection frequency by merely changing a reference clock frequency It is an object of the present invention to isolate a patient's brain wave response to a visual stimulus from surrounding environmental and artificial noise.

The above objects are accomplished by an automated visual assessment system that includes a steady state frequency locked evoked potential product detector for monitoring the steady state evoked potentials created in the patient's brain by the stimulus generator. The product detector detects the level of the steady state evoked potential signals even in the presence of substantial background noise and extraneous electroencephalographic signals. The product detector includes filters which isolate the patient's evoked potentials, a modulator which detects the response using the stimulus source frequency and a demodulator that determines the amplitude of the response. The detector can be used to monitor the evoked potential caused by visual, aural or somatic steady state stimuli.

These together with other objects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 12 depicts evoked potential amplitude during a contrast threshold test;

FIG. 13 depicts a curve of contrast threshold versus spatial frequency or a contrast sensitivity;

FIG. 14 depicts evoked potential amplitude during a color vision test;

FIGS. 15A–15C depict the initialization procedures performed by the control processor 12, supervisor microcomputer 10 and programmable analog to digital converter 14 of FIG. 1;

FIGS. 16A–16C depict the procedures performed by the control processor 12, supervisor microcomputer 10 and programmable analog to digital converter 14 during a spherical refractometry test;

FIGS. 17A–17C depict the procedures performed by the control processor 12, supervisor microcomputer 10 and programmable analog to digital converter 14 of FIG. 1 during an astigmatic axis determination test;

FIGS. 18A–18C depict the procedures performed by the control processor 12, supervision microcomputer 10 and programmable analog to digital converter 14 during an astigmatic refractive power determination test;

FIGS. 19A–19C depict the procedures performed by the control processor 12, supervisor microcomputer 10 and programmable analog to digital converter 14 of FIG. 1 during an acuity test;

FIGS. 20A–20C depict the procedures performed by the control processor 12, supervisor microcomputer 10 and programmable analog to digital converter 14 of FIG. 1 during contrast sensitivity test;

FIGS. 21A–21C depict the procedures performed by the control processor 12, supervisor microcomputer 10 and programmable analog to digital converter 14 of FIG. 1 during a color vision test;

FIGS. 22A–22C depict the procedures performed by the control processor 12, supervisor microcomputer 10 and programmable analog to digital converter 14 of FIG. 1 during a flash or transient test.

DESCRIPTION OF THE PREFERRED EMBODIMENTS

Figure 1A:
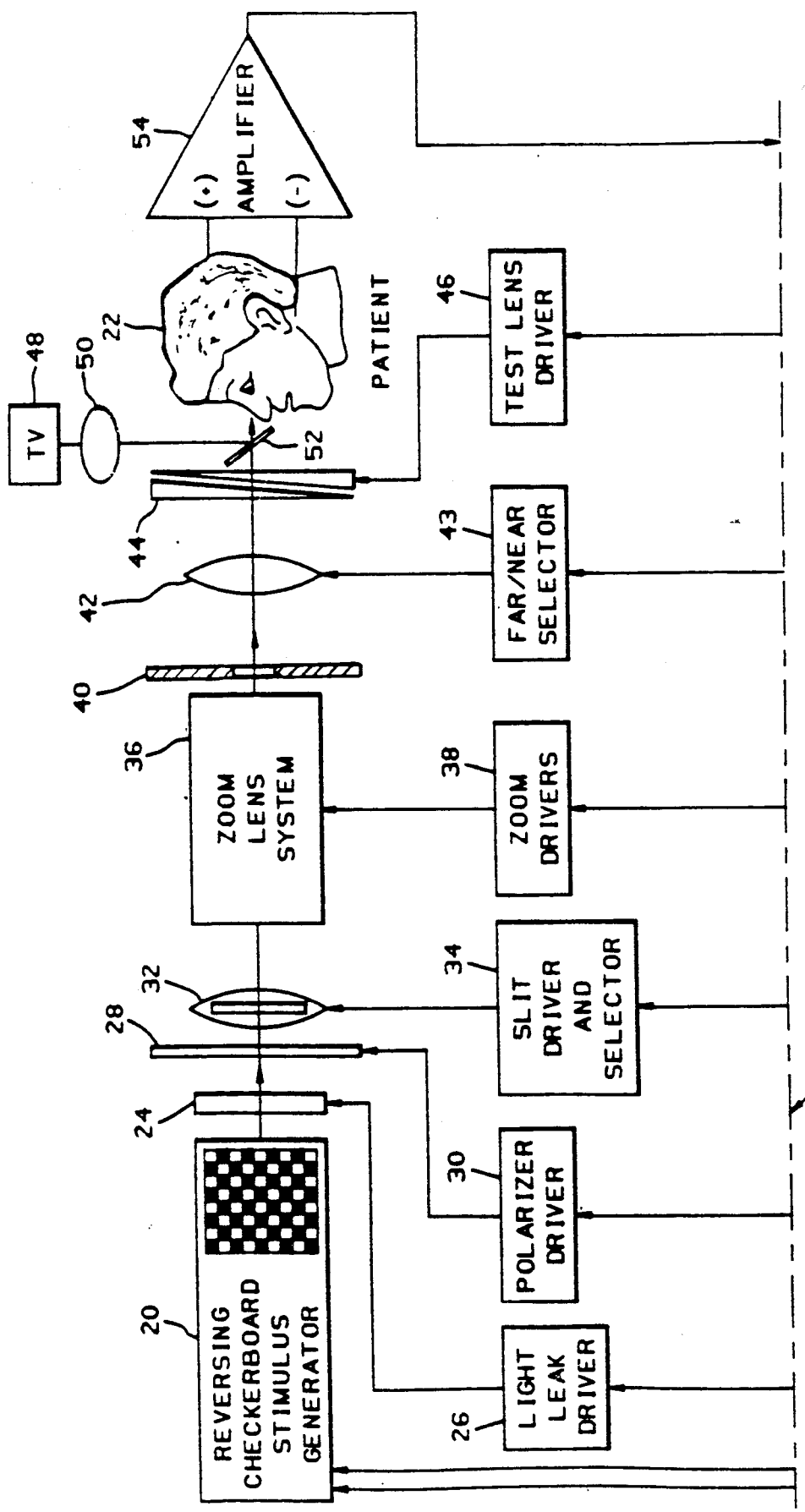
FIGS. 1A and 1B are a system block diagram of an automated visual assessment system in accordance with the present invention.

An automated visual assessment system in accordance with the present invention presents a 6 Hz reversing checkerboard pattern to a patient who views the continuously varying pattern through optic components required for a particular test. An electroencephalographic (EEG) brain wave electrode or monitor picks up the resulting evoked potential which is then amplified to a useful level. When performing some tests, the amplitude of the sinusoidal varying wave pattern is detected and during other tests, the absolute magnitude of the amplified evoked potential EEG is detected. A time varying digital value of the level of the evoked potential is interpreted in accordance with the test being performed.

Any test begins with a supervisor microcomputer 10 (FIG. 1) such as an IBM PC/XT initializing a control processor 12, such as a COMMODORE 64, and a programmable analog digital converter 14 such as a 2801 D/A board available from Data Translation of Massachusetts. The test control processor 12 positions the appropriate lenses, slits and polarizers necessary for the test through a digital input/output unit 16 such as an MW611 digital input/output board manufactured by Micro West Electronics. The control processor 12 also produces a 2.4 kilohertz control signal for driving stimulus controller 18. The stimulus controller 18 controls reversing or complementing checkerboard stimulus generator 20 to produce a visually reversing checkerboard pattern. The alternating checkerboard visual stimulus passes through the optical system to the patient 22. The optical system includes selectable and controllable lenses and filters for performing the various vision tests.

In the first embodiment, the optical system includes a counterpolarized light leak 24 and light leak driver 26, a rotatable polarizer 28 and polarizer driver 30. A rotatable slit 32 and a slit driver and selector 34, a zoom lense system 36 and zoom drivers 38, an image plane aperture 40 which defines the field of view as the zoom lense system 36 changes the apparent size of the image pattern followed by a far field lense 42 controlled by far/near selector 43. Image focus is controlled by a variable focal length lense 44 controlled by test lense driver 46. Because the human eye attempts to adapt to out-of-focus images, a television 48 is used to project an image through a far field lense 50 producing an image at infinity which is combined by an image combining half-reflecting mirror 52 with the visual stimulus from the stimulus generator and projected to the patient 22. The patient 22 produces evoked potentials in response to the stimulus and the potentials are picked up by self-preparing electrodes mounted in a head set cap, as described in U.S. application Ser. No. 822,725 mentioned in the cross-references to related applications section. The electrodes are held at positions to confront the patient's occipital lobe. In an adult, the first or lowest electrode should be positioned just above the inion, the second electrode should be positioned behind one ear and the third electrode should be positioned behind the other ear.

The evoked potentials produced by the patient and picked up by the self-preparing electrodes are conducted over an optimized shielded cable wiring system as described U.S. application Ser. No. 727,060 mentioned in the cross-references to related application section. The evoked potentials having a magnitude of from 1–10 microvolts are transmitted to a low noise, high gain shielded amplifier 54 as described in U.S. application Ser. No. 727,056.

The evoked potential signals produced by amplifier 54 are switched by switch 56 to product detector 58 or directly to the programmable analog to digital converter 14. The product detector 58 detects the amplitude of the steady state evoked potentials produced by the patient even in the presence of large-scale background noise and extraneous EEG signals. The amplitude modulated steady state evoked potential produced by the brain during certain tests includes a very strong fundamental signal at the frequency of the reversal rate of the stimulus, along with undesired harmonics, muscle movement noise and environmental noise. The product detector 58 produces the amplitude of the steady state alternating evoked potential signal free from harmonics and relatively free from noise. The programmable analog to digital converter 14 samples either the amplitude of the steady state evoked potentials from product detector 58 or the evoked potentials themselves at a number of points over a short period of time. The supervisor microcomputer 10 retrieves the samples from the A/D converter 14 and produces various test curves, combined test curves and computes test results.

Figure 2:
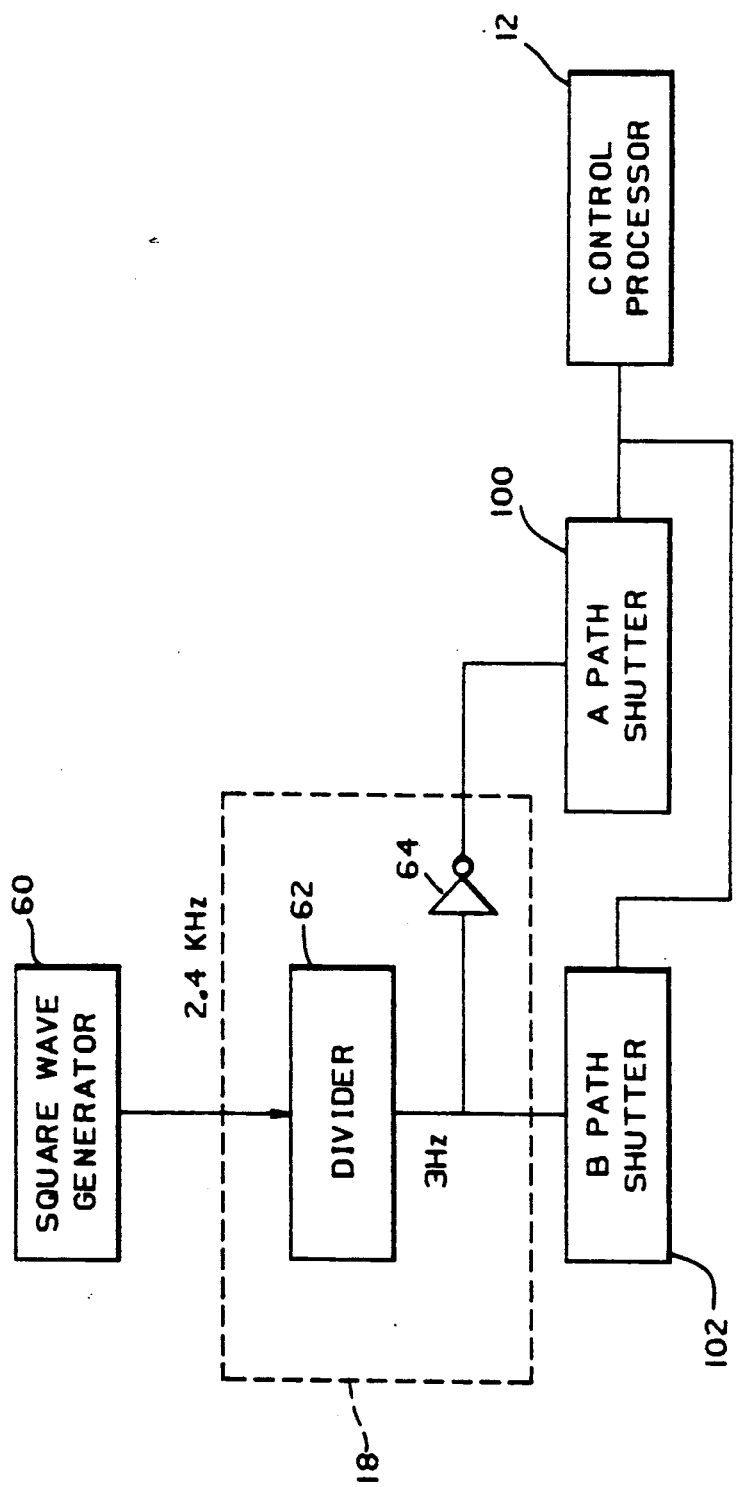
FIG. 2 depicts the details of one embodiment of the stimulus controller 18 of FIG. 1.

FIG. 2 illustrates the stimulus controller 18 when a stimulus generator having a continuous incandescent or fluorescent light source is used. A square wave generator 60 in the controller processor 12, which is included in a COMMODORE 64, produces a 2.4 KHz square wave signal which is divided by divider 62 down to a 3 Hz square wave signal. The divider 62 converts the 2.4 KHz signal down to the 3 Hz signal by dividing by 800.

Figure 3:
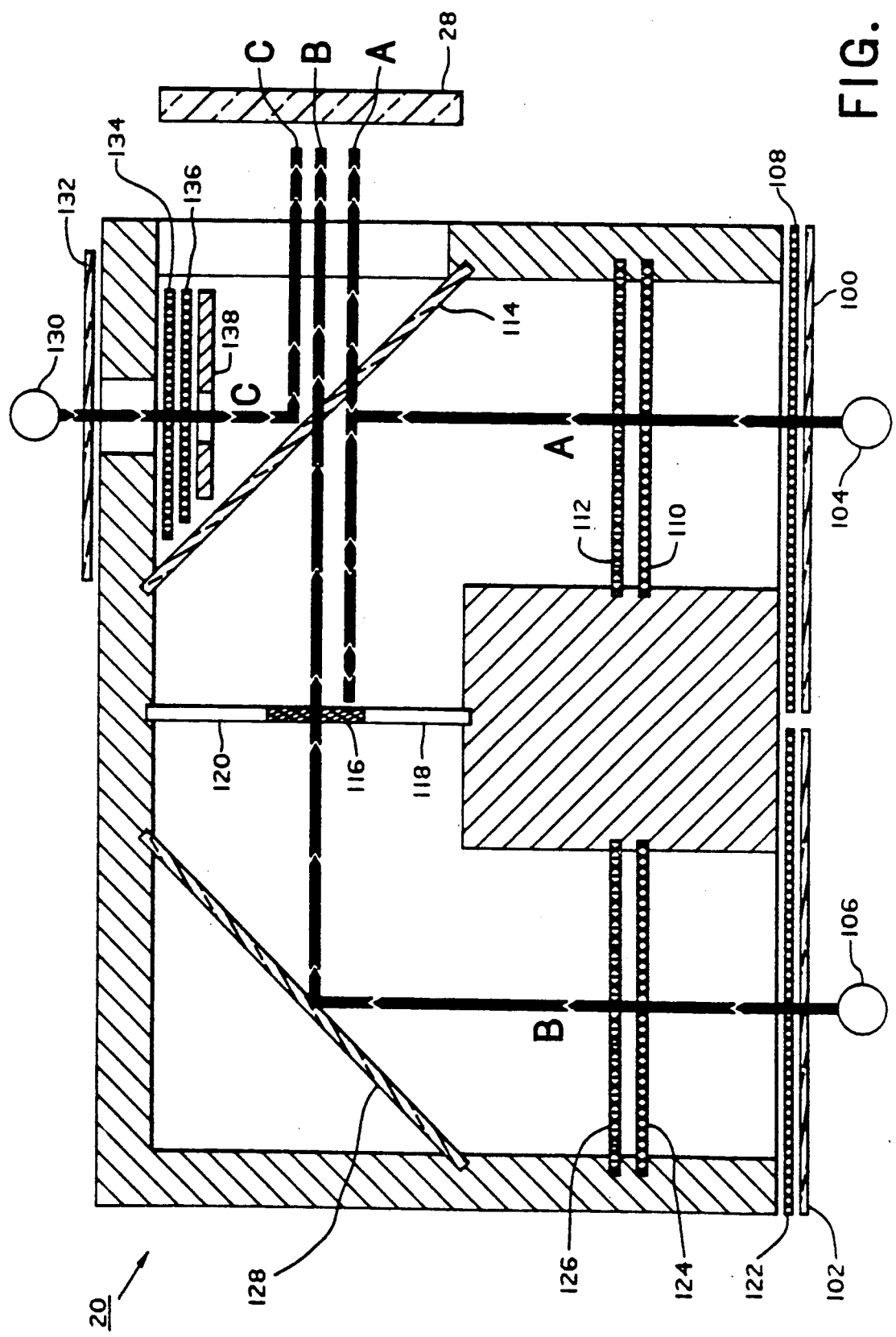
FIG. 3 is a first embodiment of the stimulus generator 20 of FIG. 1 using continuous incandescent or fluorescent light sources 104, 106 and 130.
Figure 4A:
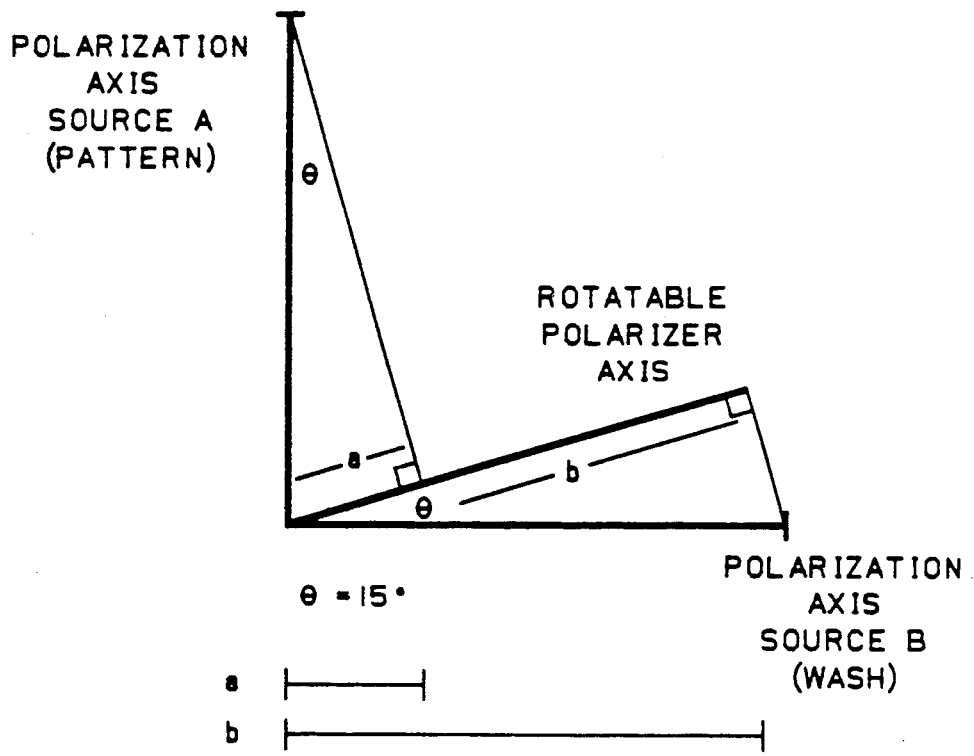
FIGS. 4A-4D depict contrast for various polarizations
Figure 4B:
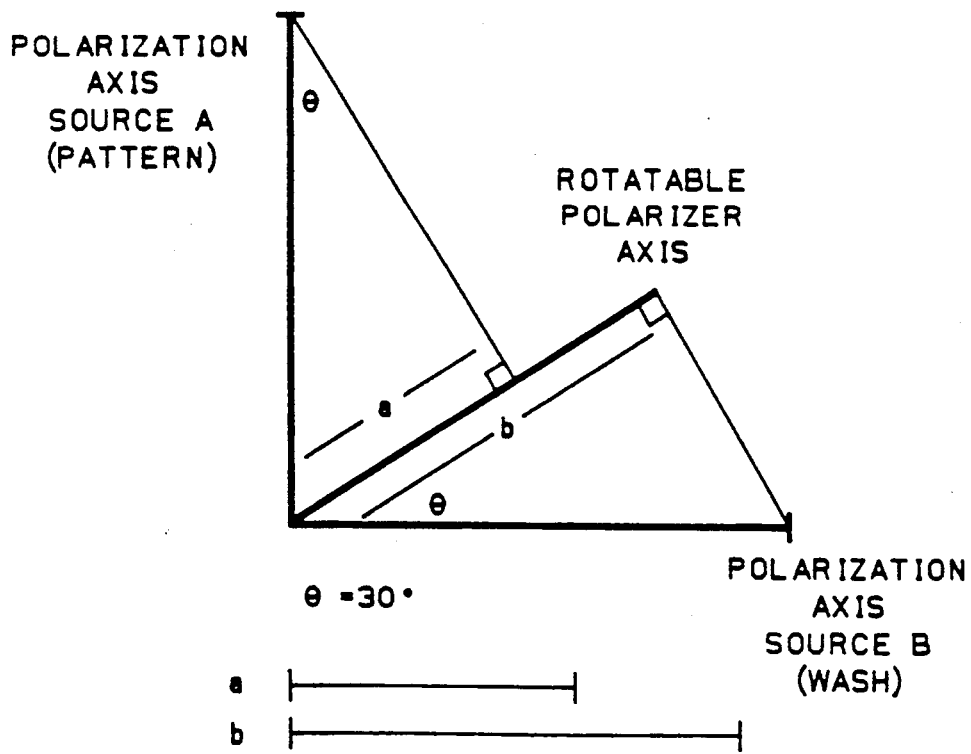
Figure 4C:
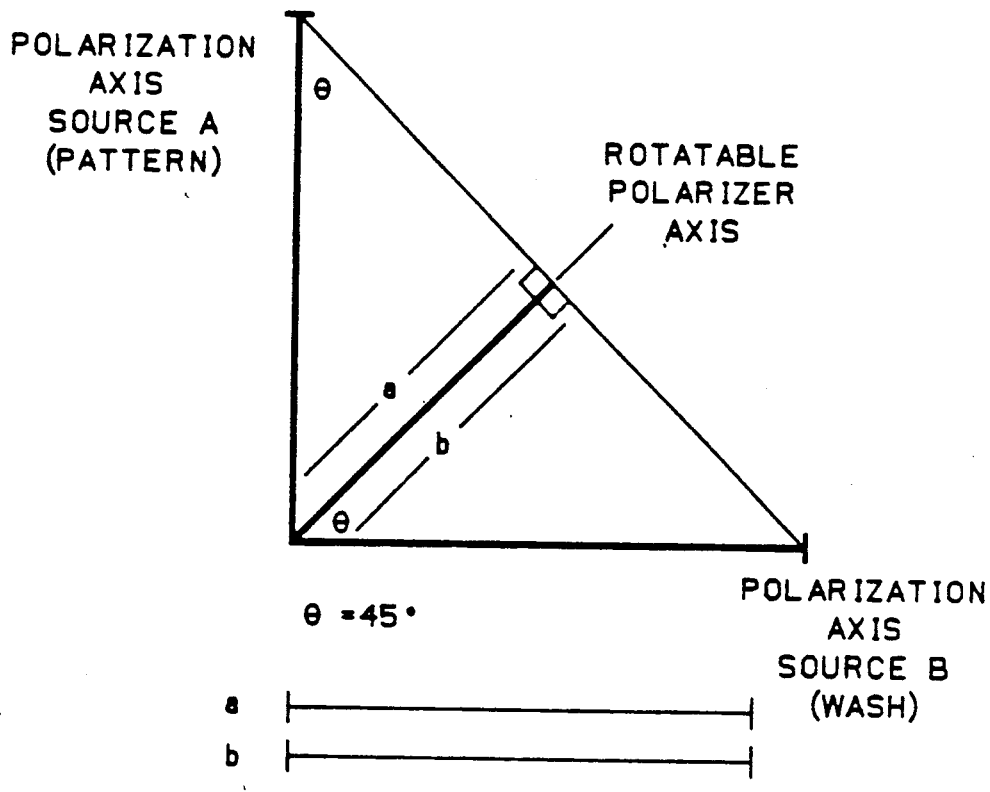
Figure 4D:
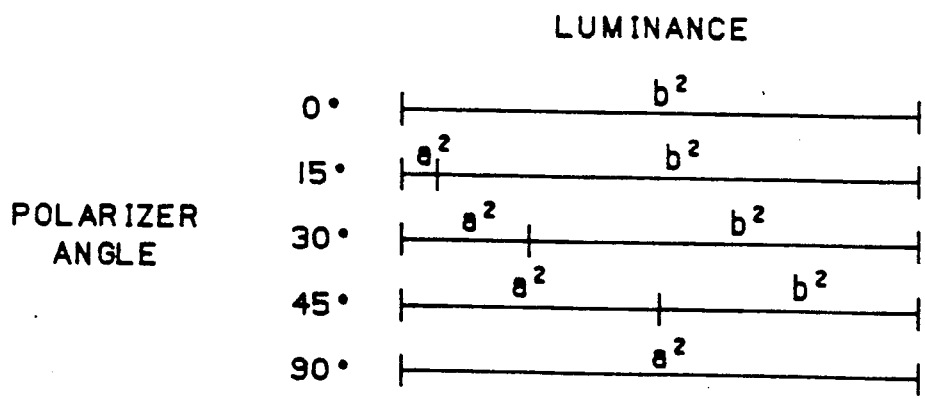

The 3 Hz signal is applied through an inverter 64 to an A path liquid crystal shutter 100 and directly to a B path liquid crystal shutter 102. The 3 Hz waveform is used to open and close the shutters 100 and 102 to produce a resultant 6 Hz stimulus transition frequency when tests requiring the alternating stimulus are being performed. In other types of tests, such as in the flash evoked potential test, the shutters are directly controlled by control processor 12. In a first embodiment of the stimulus generator 20, as illustrated in FIG. 3, light sources 104 and 106 are white light sources such as Westinghouse fluorescent bulbs called ULTRALUME bulbs which provide equal luminance (line response characteristics) in the three portions of the spectrum to Which the human eye is sensitive. The complementing or alternating pattern produced by the generator 20 is generated by alternately opening liquid crystal shutters 100 and 102 causing light to shine along equal length paths A or B, respectively. The preferred shutters 100 and 102 are available from Tektronix in Beaverton, Oregon as Liquid Crystal Color Shutters. The shutters 100 and 102 are available with a refresh and control circuit that refreshes the current state of the shutter so that it does not decay to the other state. The refresh rate must be adjusted so that the maximum transmission through each shutter is obtained when the shutter is in an open or transmissive state. The shutters 100 and 102 polarize the light passing therethrough vertically. When path A is active, light from source 104 passes through shutter 100, a matte transmission filter 108, a neutral density filter 110 and another matte filter 112. The three filters 108-112 serve to diffuse the light evenly over the light path area, so that all parts of the path are equally illuminated. The filters 108-112 are obtainable from most optical supply houses. The neutral density filter 110 is a photographic neutral density filter available from Kodak.

The diffused light traversing path A bounces off the reverse side of the beam splitter 114 and then off the mirrored portions of a checkerboard pattern mirror 116 having opaque portions 118 and 120. A suitable beam splitter is obtainable from most optical supply houses. The details of construction of the patterned mirror 116 are discussed in the Precision Patterned Mirror application listed in the Cross-References to Related Applications section. The reflected pattern from mirror 116 passes back through the beam splitter 114 to the patient 22. The light reflecting off the mirrored portions of mirror 116 appear to the patient as white while the non-mirrored portions are black whenever path A is active.

When path B is active, light from source 106 passes through shutter 102 matte filter 122, neutral density filter 124 and matte filter 126 which are the same type filters as 108-112 discussed above. The light is then reflected off beam splitter 128 and passes through the non-mirrored portions of patterned mirror 116 and through beam splitter 114 to the patient 22. The mirrored coating of the patterned mirror blocks light from path B while the non-mirrored portions of the mirror 116 pass light. As a result, the mirrored portions appear black and the non-mirrored portions appear white when light path B is activated.

To obtain equal luminance from paths A and B, the light source for one of the paths is turned on and the light intensity of the output to the polarizer 28 is measured using a light meter. The second light path is then turned on and the intensity is again measured. The neutral density filters 110 and 124 are then changed to different densities until the paths have equal luminance.

As the two light paths are alternately activated using two square waves at 3 Hz, each 180° out of phase with the other, the pattern observed by the viewer is one in which the black and white areas alternately change places, producing a transition rate of 6 Hz.

The components previously described are used when a high contrast alternating evoked potential stimulus is necessary for the vision test being conducted. When other types of tests are desired, such as a contrast test, a uniform wash field which will wash out the pattern created by the mirror can be produced. A wash light source 130 (FIG. 3) produces light which travels along path C through wash polarizer 132 which imparts a horizontal polarization to the light. The horizontally polarized light passes through matte filter 134 neutral density filter 136 and wash aperture 138. The light moving along path C then bounces off beam splitter 114 and through rotatable polarizer 28 to the patient 22. The wash aperture 138 is sized and positioned so that the light passing through the aperture 138 exactly coincides with the size of the patterned field in patterned mirror 116.

Contrast is varied while maintaining constant luminance by utilization of the effects of polarized light to control the amount of light passing to the patient 22 from the patterned mirror 116 (paths A and B), which is vertically polarized and to the patient from the wash path C which is horizontally polarized. This is accomplished by turning the rotatable polarizer 28.

Basic to the understanding of how the contrast changes are produced by the generator 20 is the fact that light is passed by polarizers with parallel axes of polarization and blocked by polarizers with perpendicular axes of polarization As a consequence, when rotatable polarizer 28 is in a position such that its axis of polarization is vertical, the light from the patterned mirror 116, which has a parallel vertical polarization, passes through the rotatable polarizer 28 to the patient 22 while the light from the wash source 130 has a perpendicular horizontal polarization and is blocked. In contrast, when the rotatable polarizer 28 is in a position such that its axis of polarization is horizontal, the light from the patterned mirror 116 has a perpendicular polarization and is blocked, while the light from the wash source 130 has a parallel polarization and passes through the polarizer 28 to the patient 22. In intermediate polarizer positions, an intermediate amount of light from each source is passed to the patient 22. If the average luminance of both the patterned and wash fields is equal, then the luminance observed by a patient 22 will be constant as the rotatable polarizer 28 is rotated.

The physical effects which lead to constant luminance contrast variation are illustrated in FIGS. 4A-4D. The physical basis for this effect is that the amplitude of light produced by a polarized light source which passes through a second polarizer is equal to the vector projection of the polarized source amplitude onto the axis of the rotatable polarization. Thus, with two perpendicularly crossed polarized sources of equal strength, $A=B$, the light amplitude contributed by sources A and B is $a = \sin\theta$ and $b = \cos\theta$. Luminance equals amplitude squared or $a^2 + b^2$ equals average luminance. Substituting, we get average luminance equals $(\sin\theta)^2 + (\cos\theta)^2$, noting that $(\sin\theta)^2 + (\cos\theta)^2 = 1$ indicates that average luminance must be constant. In the above equation, $\theta$ is equal to the angle between the wash 132 and rotatable polarizer 28 axes. The above example demonstrates that the value of the average luminance is a constant regardless of the relative polarizer angle and the resulting contrast variation.

The provision of a constant luminance source throughout a vision test is of critical importance to vision testing because the response of the human visual system varies depending on luminance. A constant luminance is necessary throughout a vision test for accurate results to be produced.

To perform a color vision test, the stimulus generator of FIG. 3 must have included therein appropriate colored filters inserted in paths A through C. For example, when a red/green color vision test is performed, a red filter is inserted in paths A and B while a green filter is inserted in path C. The mechanical insertion of the appropriate filters and conducting the color vision test for each pair of colors can be cumbersome and time consuming. As an alternative, color shutters that use dichroic filters are available from Texas Instruments.

Figure 5:
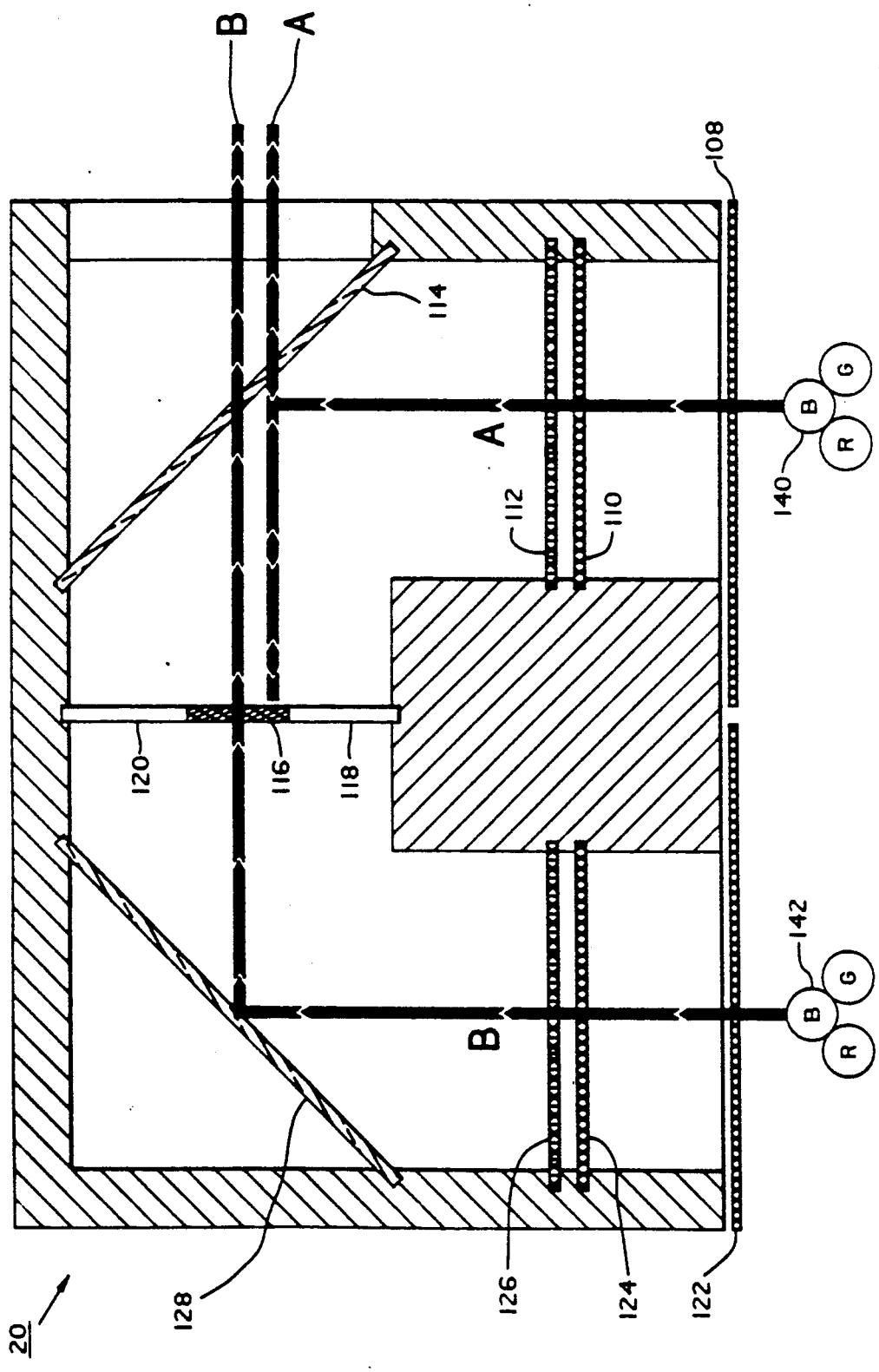
FIG. 5 depicts a second embodiment of the stimulus generator using tricolored light emitting diode arrays or fluorescent lamps 140 and 142 as the light source.

An alternate embodiment of the stimulus generator 20 of FIG. 3 which uses colored light emitting diodes or fluorescent lamps are illustrated in FIG. 5. Tricolored light source arrays 140 and 142 are substituted for the sources of FIG. 3. These light emitting arrays, if constructed of diodes, are constructed from red and green diodes, manufactured by Hewlett Packard and blue diodes, manufactured by Seimens Each of the diodes must be adjusted as to intensity using, for example, adjustable resistors, so that all the diodes produce the same intensity light. This can be performed by turning on all the diodes and adjusting color intensity of the colors until the whitest light is produced by the generator. The diodes are arranged in a uniform array pattern in a closely bunched configuration similar to the groupings of color phosphor dots on a colored television screen. If colored fluorescent tubes are used, they are placed side by side. The use of the tricolored light sources 140-142 allows the removal of the liquid crystal shutters 100 and 102.

Figure 6A:
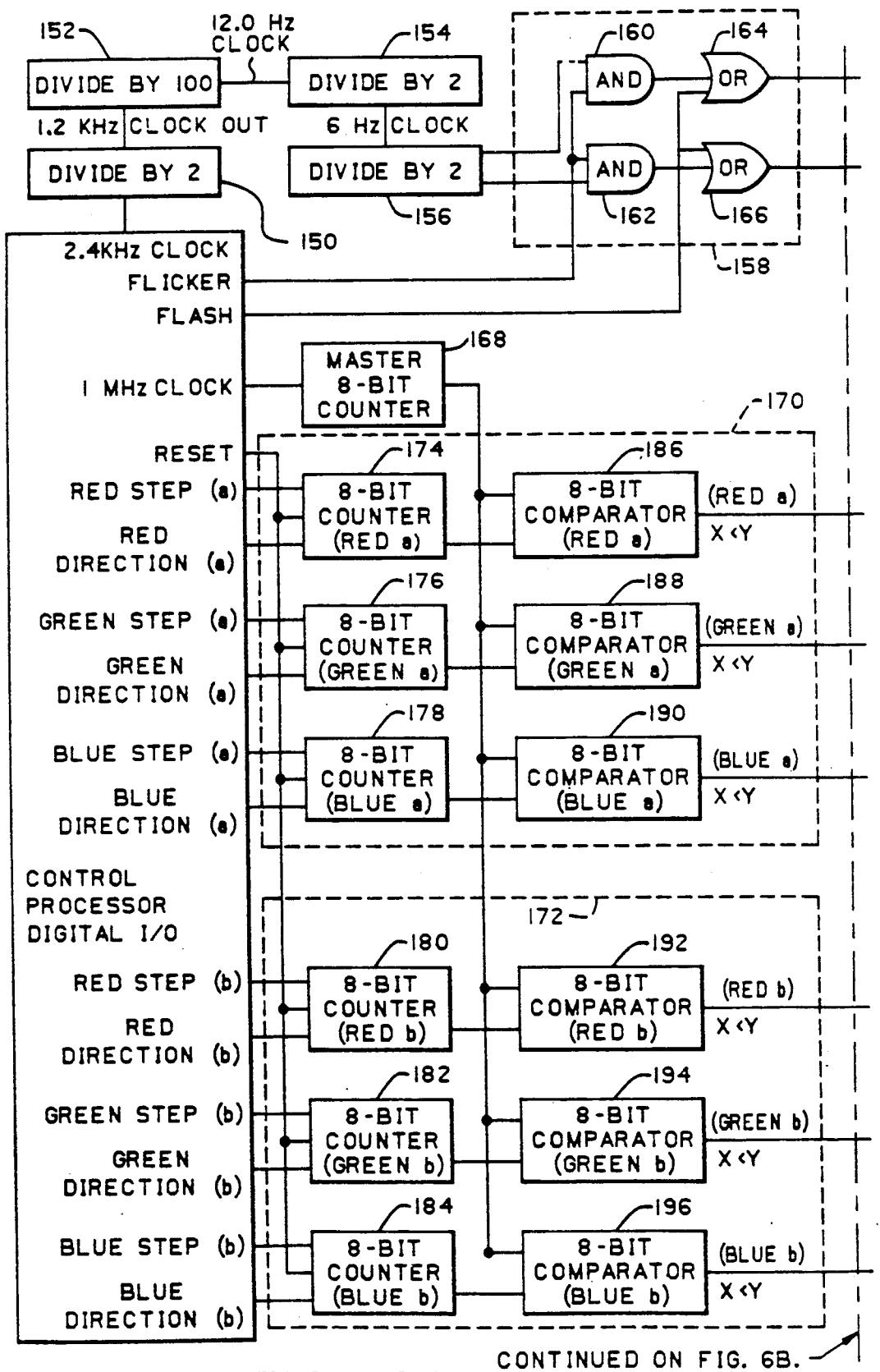
FIGS. 6A and 6B are a circuit diagram for the stimulus controller 18 of FIG. 1 when the stimulus generator of FIG. 5 is used.
Figure 6B:
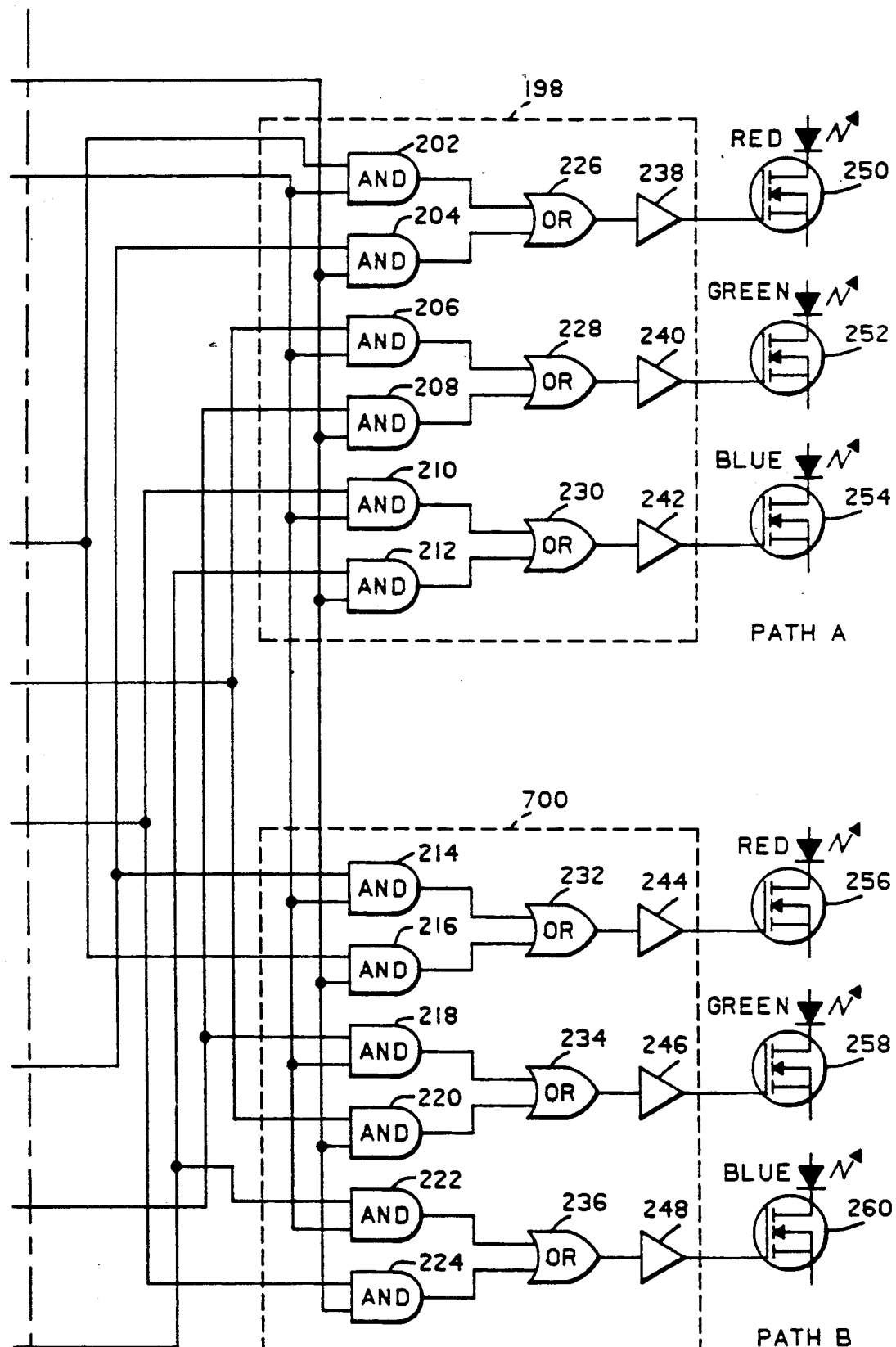

The use of tricolored light sources in the stimulus generator 20 requires the provision of a different stimulus controller than that depicted in FIG. 2. FIG. 6 depicts the stimulus controller 18 necessary for the light emitting diode array embodiment of the stimulus generator 20. This stimulus controller 18 pulse width modulates the diodes with the on time equal to the pulse width. The duty cycle has 256 parts and the clock frequency is 1 MHz. FIG. 6 discloses a circuit for controlling the A and B paths which can be divided into appropriate subunits. The 2.4 KHz clock signal from control processor 12 is divided down to produce two 3 Hz signals by dividers 150-156. These dividers produce color selection signals for the two paths through a flicker/flash control circuit 158. The control circuit 158 is controlled by a flicker and flash enable signal from the test control processor 12 and digital input/output board 16. The flicker/flash control circuit 158 includes AND gates 160 and 162 which allow the flicker clock to pass therethrough when enabled and OR gate 164 and 166 which produces a flash enable signal whenever the flash signal line is at a high level.

The control circuit of FIG. 6 allows the amplitude of the red, green and blue sources to be continuously varied so that any desired color and amplitude for that color can be produced. A master 8-bit counter 168 is used to produce a reference time period which is segmented into appropriate on and off portions for the various colored diodes. The color control circuits 170 and 172 include color counters 174-184 which are incremented in accordance with the magnitude of the color desired. The contents of the color counters 174-184 are compared by 8-bit comparators 170-196. Whenever the color counter input (from 174-184) is greater than the output from the master counter 168, the appropriate color diode for the path is activated through activation circuits 198 and 200. The activation circuits 198 and 200 include AND gates 202-224 which pass the color activation signals from circuits 170 and 172 whenever the appropriate enable signals are provided by the flicker/flash control circuit 158. The resulting light emitting diode control signals are passed through OR gates 226-236 to current amplifier 238-248. The amplifiers provide sufficient current to drive the color diodes 250-260 for paths A and B.

During a color vision test, one of the colors should remain at constant intensity while the opposite color varies in intensity. For example, during a red/green test, the red diodes would have a duty cycle of 100% (on all the time) while the green diodes in both paths A and B would start at a 50% duty cycle and be swept in opposite duty cycle directions.

During a contrast test, the duty cycle of all three colors is varied. As an example, the color signals a and b could both be set at 50% providing a half power intensity light and zero contrast. During the first half of a complete cycle, the color signal a would be applied to path B while the color signal b would be applied to path B. During the second half of a complete cycle, the color signal a would be applied to path B while the color signal b would be applied to path A. As the duty cycles of color signals a and b separate, for example, a moving toward 25% and b moving toward 75%, the contrast is increased. The present invention allows the start of the contrast test at any light intensity, for example, the duty cycle of both signals at zero contrast could be set at 75% and one signal moving toward 50% while the other toward 100%. The present invention will allow a contrast test of persons with partially obscured vision such as a person having cataracts.

Figure 7:
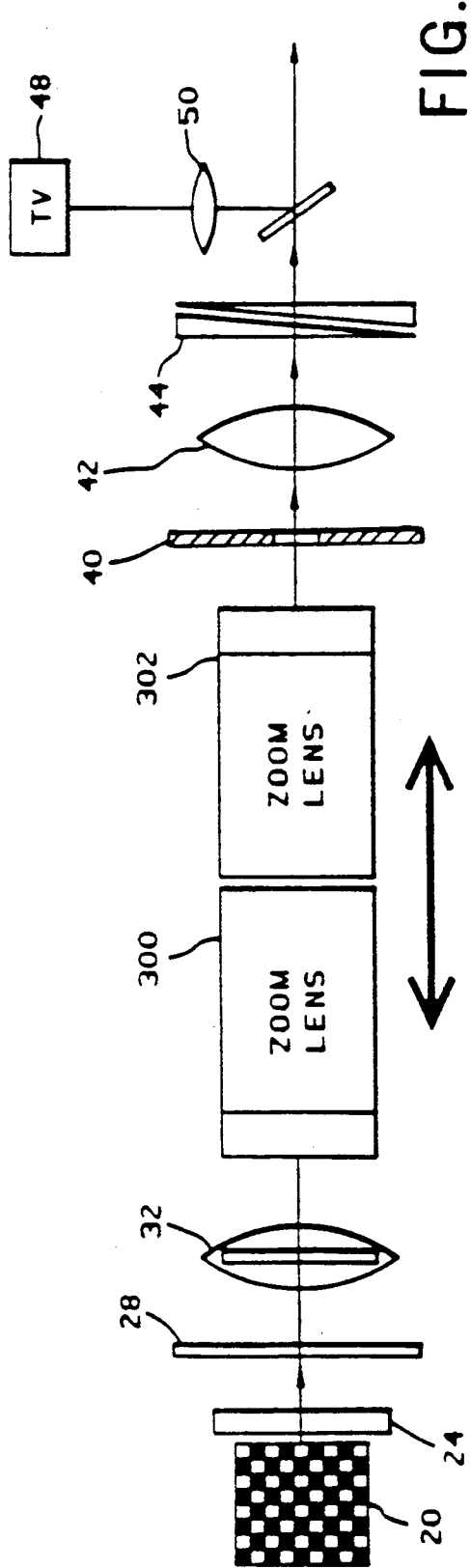
FIG. 7 is a detailed version of the system optics when the stimulus generator of FIG. 3 is used.

Once the visual stimulus leaves the stimulus generator 20, it passes through a lense system that provides a constant image size to the patient's retina so that variation in stimulus pattern size on the retina do not cause variations in the amplitude of the evoked potential. The lense system effectively provides a continuously variable focus lense which has zoom capability so that image size can be changed to allow spatial frequency or acuity to be tested. When the light leaves the generator 20, as illustrated in FIG. 7, that is, the generator that uses a white broad spectrum light source, it pauses through counter polarized light leak 24, rotatable polarizer 28 and slit 32 if the stenopic slit has been selected. Next, the visual image encounters the first of two zoom lenses 300 and 302, which are arranged in mirror symmetry, that is, the lenses face each other. Each zoom lense can be a Nikon zoom lense which provides a range of 35 to 105 mm. The zoom lenses 300 and 302 are locked together during refractometry tests so that a constant total lense length is provided. The zoom lense 300 is placed so that the focal plane (the plane where the film would normally rest) is coincident with the mirror 116. When the size, spatial frequency or apparent size of the checks on the checkerboard stimulus are changed, one of the lenses is held constant while the other lense is driven. Once the image leaves the second zoom lense 302, it passes through an image plane aperture 40 which ensures constant image size and then through a far field lense 42 such as an auto Nikon 50 mm lense. During any apparent image size change, the aperture 40 maintains a constant field of view for the stimulus image, thereby preventing evoked potential changes due to varying image size on the patient's retina. The far field lense 42 places the image at infinity no matter the focus of the image.

The image then passes through a variable focal length lense 44 which is capable of traveling from minus 7 to plus 7 diopters. The computer controlled variable focal length lense 44, available from Humphrey Instruments of San Leandro, Calif., acts as a test lense which is changed in focus thereby changing the amplitude of the evoked potential produced by the patient 22. The Humphrey lense is a two element lense and if the elements are displaced along the horizontal axis, the spherical power of the lense is changed and if displaced along the vertical axis, the cylindrical power is changed.

The alternating stimulus image is then combined with a video image which can be a cartoon when a child is being tested or an eye care educational film when an adult is being tested. The video image is also placed at infinity by far field lense 50 which can also be a Nikon 50 mm lense. At the beginning of each test, the patient 22 adjusts the far field lense 50 so that the video image is in focus providing an eye reference image. When the video image and the stimulus generator image are combined, the stimulus generator image only occupies a small portion of the image presented to the patient and the patient should primarily be watching the video image. Since the video image is at infinity and the alternating stimulus only occupies a small portion of the total image presented to the patient, the patient's eye does not attempt to adapt to the changing focus stimulus generator image, that is, the video image is a reference image that prevents eye adaption.

Figure 8:
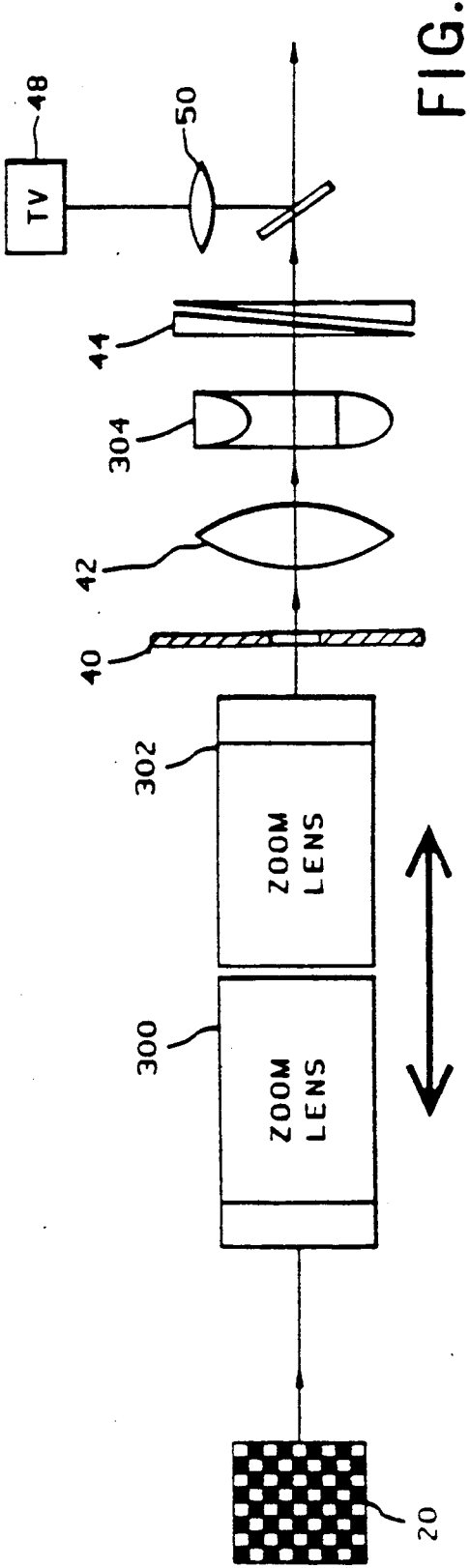
FIG. 8 is a detailed diagram of the system optics according to the present invention when the stimulus generator of FIG. 5 is used.

FIG. 8 is the image projection system when a generator 20 using the light emitting diode array or fluorescent tubes is provided. The second version of the lense system adds a cylindrical lense 304. The cylindrical lense 304 is used to perform astigmatic tests and is available from Bausch and Lomb of Rochester, N.Y.

The evoked potentials produced by the patient 22 are picked up by self-preparing monitors mounted in electroencephalographic cap which can be modeled on a baseball cap so that the patient will not be intimated. In the alternative, the monitors can be mounted in a head set or in a lightweight electrode carrier that fits on the back of the skull and described in U.S. application Ser. No. 822,725. A self-preparing monitor is an electrode which penetrates a keratinous (dead) layer of skin to contact an underlying epidermis layer without causing bleeding The monitor is shielded and if the cap version for carrying the monitor is used, a shield dome which covers the head is provided. The shielding of the monitor and head surface reduces environmental electromagnetic noise. The evoked potentials picked up by the self-preparing monitors are conducted over an optimized shielded cable system, as previously mentioned, which has as small a loop capture area as possible to reduce unwanted noise.

The low noise evoked potentials, having a magnitude of from 1 to 10 microvolts, are transmitted to a low noise high gain shielded amplifier, as previously mentioned and identified in the cross references section. The amplifier is a differential amplifier providing a gain of approximately $10^6$ and a common mode rejection of 85 dB. The amplifier is a completely shielded amplifier which provides signal clipping to prevent damage by large amplitude signals. The amplifier includes bandpass filters to remove unwanted noise.

Figure 9:
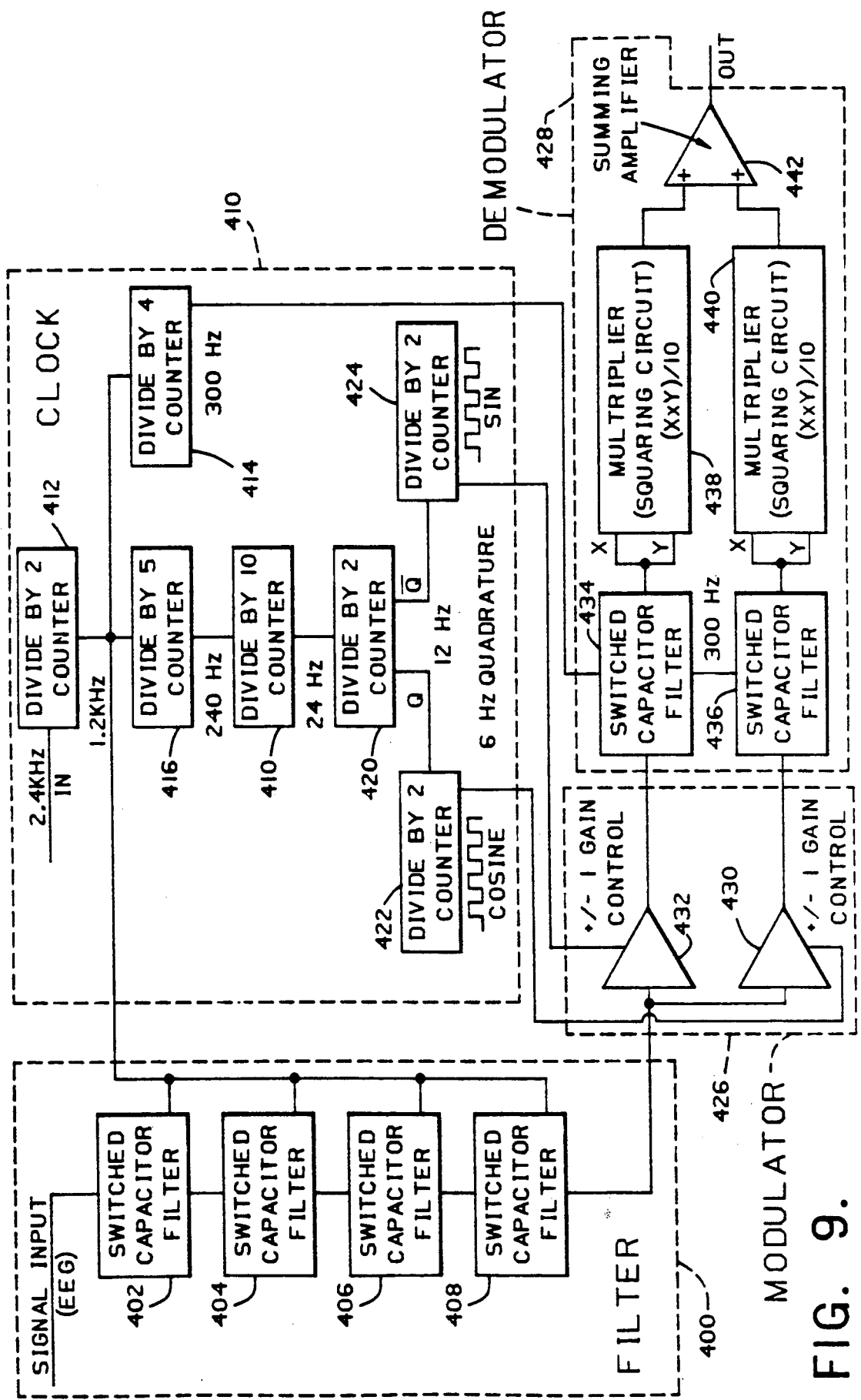
FIG. 9 is a detailed diagram of the product detector 58 of FIG. 1.

Once the evoked potentials are amplified, they pass through switch 56 which allows the evoked potential signals to be connected directly to the programmable analog digital converter 14 or to product detector 58, the details of which are illustrated in FIG. 9. The product detector 58 essentially provides amplitude demodulation of the 6 Hz evoked potential signal which is amplitude modulated by varying the focus of the test lense using the frequency (6 Hz) of the stimulus source as a locking frequency for performing the demodulation.

The detector 58 is provided with both the EEG signal from the patient 22 and a 2.4 KHz clock signal from the control processor 12. The steady state EEG signal is passed through a filter section 400 including a series of switched capacitor filters 402–408 synchronized with a clock signal having the same frequency as the stimulus source. Each switch capacitor filter can be an EEG Reticon filter model 5620. The filters 402–408 are bandpass filters having a center frequency of 6 Hz and a bandpass of approximately 1 Hz. Internal detector clock signals are provided by a clock 410 from the 2.4 KHz clock signal from the control processor 12. The clock 410 includes counters 412–424 which provide not only the clock signal for the filter 400 but also clock signals for modulator 426 and demodulator 428. The evoked potential signal is fed to a sine/cosine square wave modulator 426 where the signal is split into two paths. One path provides cosine square wave multiplication through switched amplifier 430 and the other path amplifier 432 provides sine square wave multiplication. That is, the gain of each amplifier is turned on in synchronism with the corresponding half-wave of the modulated evoked potential signal. The amplifiers each can be an operational amplifier such as a 3140 manufactured by RCA, controlled by a quadbilateral switch model DG201 from Siliconix of Santa Clara, Calif. making the amplifiers gain switching amplifiers.

The modulator 426, during the amplitude modulation, produces side band frequencies at the sum and difference frequencies of the input signal and the modulating wave. If the modulating wave and the stimulus wave are of equal frequency, the signals on the input line that are of equal frequency to the stimulus clock will have a DC level shift at the output of the modulator 426 proportional to the level of the desired frequency component of the input signal. The signals are then passed to switched capacitor filters 434 and 436 in the demodulator 428. The switch capacitor filters 434 and 436 can be the same type filters as discussed previously. The switched capacitor filters 434 and 436 remove all signal components above 1.5 Hz, thus confining the signal of interest to the approximately DC (difference frequency) component of the outputs of the modulator 426. The DC component corresponds to the level of the patient's response to the stimulus (the focus, the contrast, etc.).

At this point during evoked potential signal processing, any change in the desired signal level or phase also results in momentary changes in the frequency of the signal. Both of these type changes are going to occur in an evoked potential system and will cause undesirable variation in the DC level of the signals produced by the modulator 426 when either output is measured independently or as a simple sum This problem is resolved by utilizing the effects of a trigonomic identity $\cos^2 + \sin^2 = 1$. That is, the sum of the squares of the amplitude of the sine and cosine modulated signals is equal to the amplitude of the original signal. The squaring of the modulated signals in each path is provided by analog multipliers 438 and 440 such as Burr Brown amplifiers having model number 4206K. The signals from the multipliers 430 and 438 are combined by a summing amplifier 442, such as a 741 operational amplifier, manufactured by RCA, to produce the amplitude of the evoked potential signal.

A reference product detector can also be added to the system and set at a detection frequency such as 5 Hz. The reference product detector would provide a baseline for brain wave activity from which the evoked potential signals at 6 Hz can be measured When the reference detector is used, the outputs of the 6 Hz detector and the reference detector would be combined using a differencing amplifier to produce an absolute evoked potential signal. It is also possible to provide a second reference detector detecting at a frequency above the stimulus frequency. In effect, the reference detectors allow the background brain activity to be removed from the signal of interest.

The amplitude signal produced by the detector 58 or amplifier 54 is sampled by the A/D converter 14 every 100 microseconds and the microcomputer 10, as discussed in more detail later, performs a low path linear recursive filter function on the samples and displays the resulting curve. The curve is then used to diagnose various visual functions.

Figure 1B:
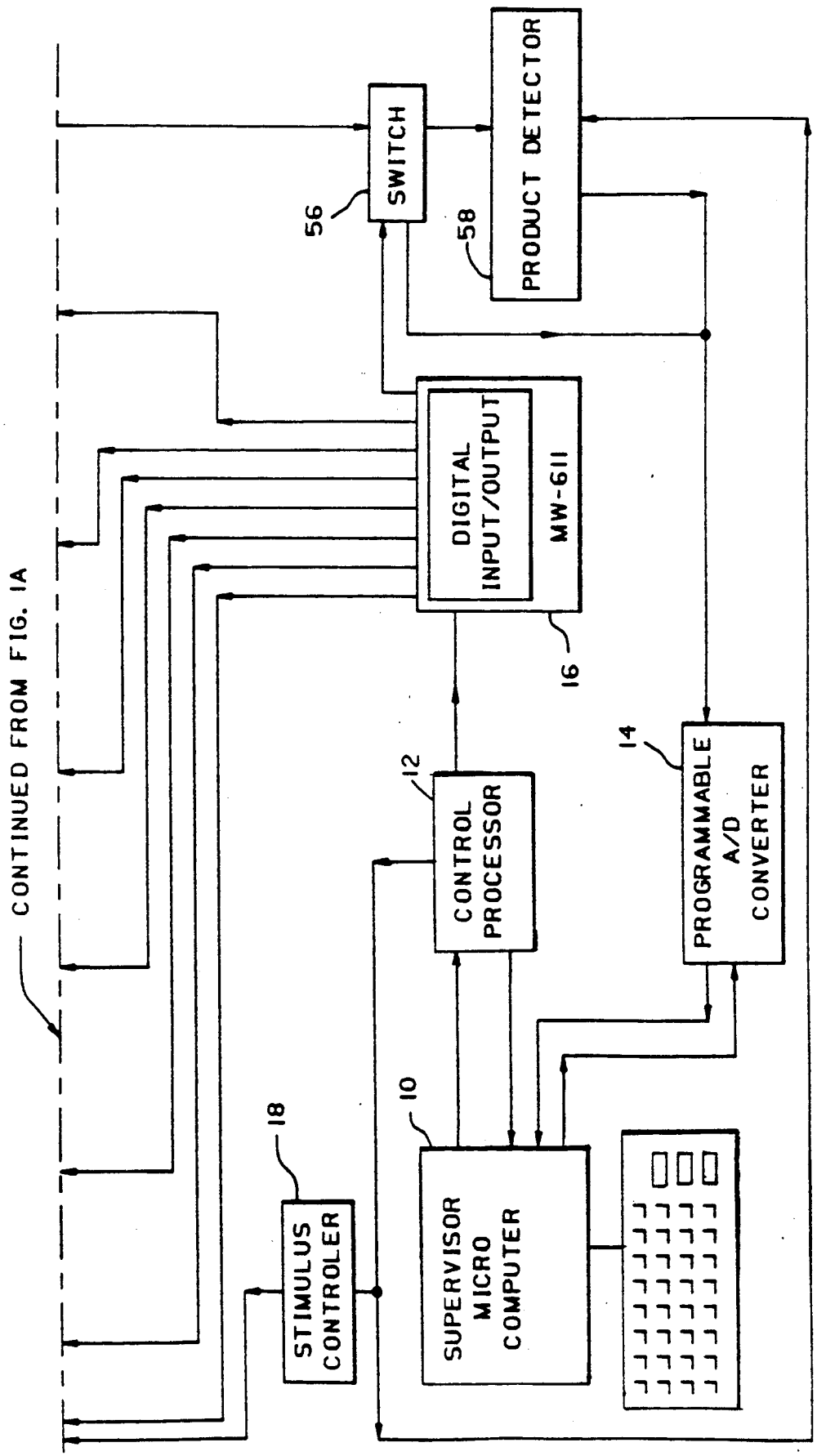

The lense, polarizer and slit drivers 26, 30, 34, 38 and 46 of FIG. 1 comprise stepper motors, such as Model M03 by Slosyn of Superior Electric, Bristol, Conn. driven by up and down pulses supplied from the control processor 12 and coupled to the lenses, etc., through gear reduction drives and driver control circuits Each driver control circuit includes an up-down counter which counts the pulses from processor 12 and a read-only memory which converts the count to four-position signals which are applied to the stepper motor through a buffer and Darlington power transistors The details of the lense drivers can be found in co-pending U.S. Pat. application No. 727,032.

The lense selectors 34 and 43 are solenoid operated via a binary control signal from the control processor 12 amplified by a Darlington power transistor and used to switch a relay that drives a standard solenoid having a solenoid drive power source. These selectors (solenoids) are two-position selectors, that is, the respective optical device is either positioned in the stimulus path or completely out of the stimulus path.

Figure 10:
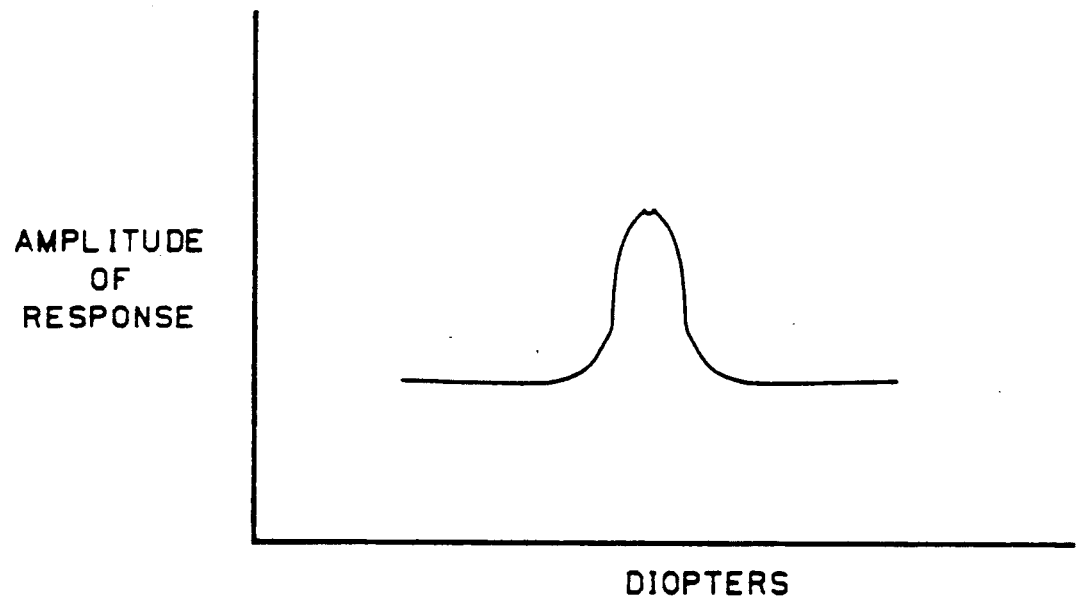
FIG. 10 depicts evoked potential amplitude during a spherical refractometry test.

The system of the present invention can be operated to perform several different tests. Each test takes from 5 to 7 seconds, resulting in a system that minimizes the amount of time necessary for testing vision. The first test is a spherical refractometry test which tests both near and far vision. For the far vision test, the patient views the stimulus through the variable focal length lense 44, far field lense 42 and zoom lense system 36. The far field lense 42 and zoom lense system 36 place the image at infinity. For the near vision test, the far field lense is removed and the patient views the stimulus through the variable focal length lense 44 and zoom lense system 36. Each test consists of continuously sweeping the strength of the variable focal length lense 44 by rotating the stepper motor in the test lense driver 46 while monitoring the amplitude of the response through the product detector 58 and programmable analog to digital converter 14. The lense 44 preferably starts at a positive maximum correction value and sweeps to the maximum negative correction value. The converter 14 converts the analog values into digital values which supervisor microcomputer 10 interprets as the level of the response. The response will peak at the optimum lense refraction power or the diopter which properly corrects the focus of the patient's eye as illustrated in FIG. 10. When reference product detectors are used, the resulting brain wave activity reference curve is subtracted from the evoked potential curve, producing an absolute evoked potential curve. This curve is displayed by the supervisor microcomputer 10 as will be discussed in more detail later.

Figure 11:
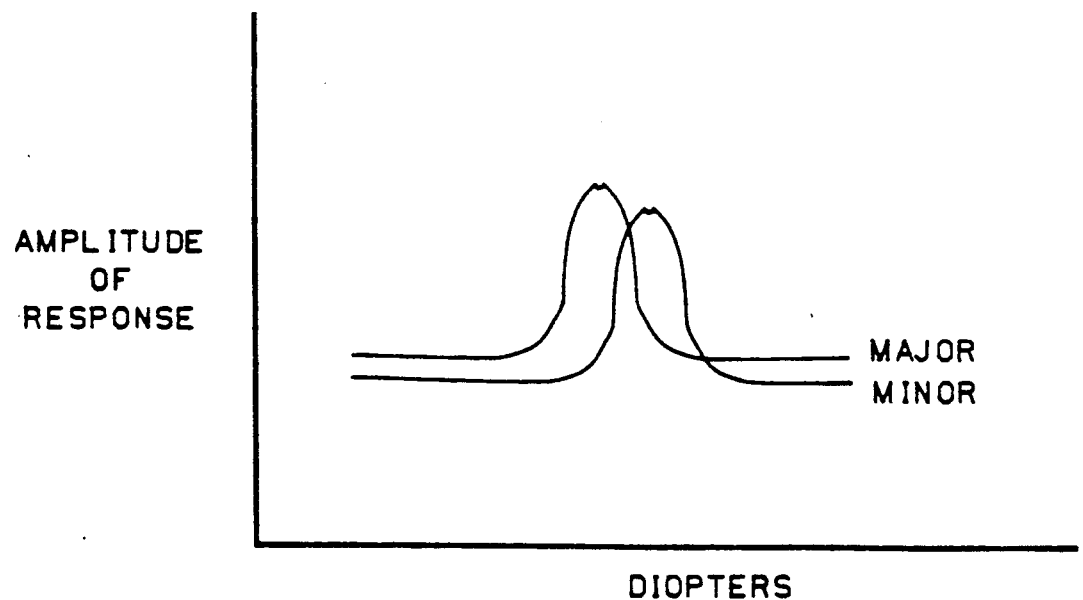
FIG. 11 depicts evoked potential amplitude during an aspherical refractometry test.

When the aspherical refractometry test is performed, the rotatable slit 28 is positioned between the stimulus generator 20 and the patient 22 to present a slit version of the alternating checkerboard pattern. An alternative is to provide the rotatable variable focal length lense 304 having cylindrical correction capability. This test consists of first determining the far vision spherical correction as previously discussed and then with the variable focal length lense 44 set at this value rotating the slit while monitoring the value of the evoked potential. The angle of the slit at which the maximum value is detected corresponds to the major axis of stigmatism. The far field refractometry test is then repeated with the slit in this position and at a position perpendicular to this one. The resulting maximum values correspond to the proper diopter values for spherical correction. If a cylindrically adjustable lense is used in place of the variable focal length lense, the measured spherical correction is divided between the spherical and cylindrical nodes of the lense and, as with the slit, the lense is rotated to determine the axis of stigmatism. The curves produced in this test are illustrated by FIG. 11.

During a contrast sensitivity test using one embodiment of the generator 20, the alternating stimulus image produced by the checkerboard mirror 116 is washed out by rotating polarizer 28 to a position which allows only light from path C to reach the patient while light from paths A and B is blocked, and by varying the intensity of the tricolored sources 140 and 142 in the second embodiment. The contrast threshold test is performed by first placing a far field focused image on the patient's retina through the zoom lense system 36, far field lense 42 and variable focal length lense 44 based on the diopter for correction previously determined. The image is provided at a first spatial frequency. The polarizer 28 is rotated (or the intensity produced by tricolor sources 140 and 142 is changed) from a position of zero contrast to a position of maximum contrast while monitoring the evoked potential. That is, the polarizer is rotated from alignment with the polarization of the wash source 144 to the polarization of the mirror sources 140 and 142. The curve produced by the monitored evoked potential from the product detector after low pass filtering, will have a base line as illustrated in FIG. 12 followed by a rapid rise in recorded level. A linear regression fit of the rising area of the curve will produce an X axis intercept for the effective contrast sensitivity for the stimulus at the spatial frequency currently viewed. The test is repeated at several different spatial frequencies to plot a contrast sensitivity curve as illustrated in FIG. 13. The spatial frequency of the image is changed by adjusting the focal length of one of the zoom lenses 300 or 302 in the zoom lense system 36.

A color vision test is performed using the stimulus generator of FIG. 3 by replacing the normal black/white shutters 104 and 106 with either red/green or blue/green polarized shutters and replacing the rotatable polarizer 28 with similar red/green or blue/green polarizers if the first embodiment of generator 20 is used. If the stimulus generator of FIG. 5 (the second embodiment) is used, the color variations are created by controlling the intensity of the diodes in the light emitting diode arrays 140-144. The test is conducted in the same manner with the first embodiment as that for contrast sensitivity except that the polarizer 28 is only rotated 45 degrees and the intensity of the colors rather than the contrast is varied. A color deficiency at a particular intensity is indicated by a pronounced dip in the amplitude curve as illustrated in FIG. 14.

Acuity tests are performed by placing the alternating image in focus through the variable focal length lense 44 and far field lense 42 at an image size which is detectable by the patient 22. The zoom lense system 39 is then used to present a constant field of view, variable spatial frequency, fixed luminance image of the stimulus by adjusting the focal length (the magnification) of one of the zoom lenses to present a progressively smaller stimulus image to the patient until the image is no longer Visible to the patient. That is, the image is reduced until the evoked potential signal disappears. As with contrast sensitivity, the linear regression axis intercept of the rise in the curve represents the acuity limit.

During the transient pattern evoked potential test, the patient 22 views a reversing pattern and the evoked potential signal produced by amplifier 54 is provided directly to the programmable analog digital converter 14 by switch 56. During this test, the control processor 12 controls the shutters or tricolor light sources to present single reversal flash to the patient instead of a steadily flickering pattern. The light sources for the mirror are changed from, for example, the A path to B path a single time. The supervisor microcomputer acts as a signal averager to detect latency effects produced by the patient's visual system.

A flash evoked potential test can be conducted by flashing the wash source or both tricolored light sources a single time. This test also allows the latency of the patient's visual system to be observed.

FIGS. 15-22 illustrate the procedures performed by the supervisor microcomputer 10, control processor 12 and programmable analog to digital converter 14 during the tests previously discussed, and how the procedures executed by these intelligent devices interrelate and communicate.

Figures 15A, 15C:
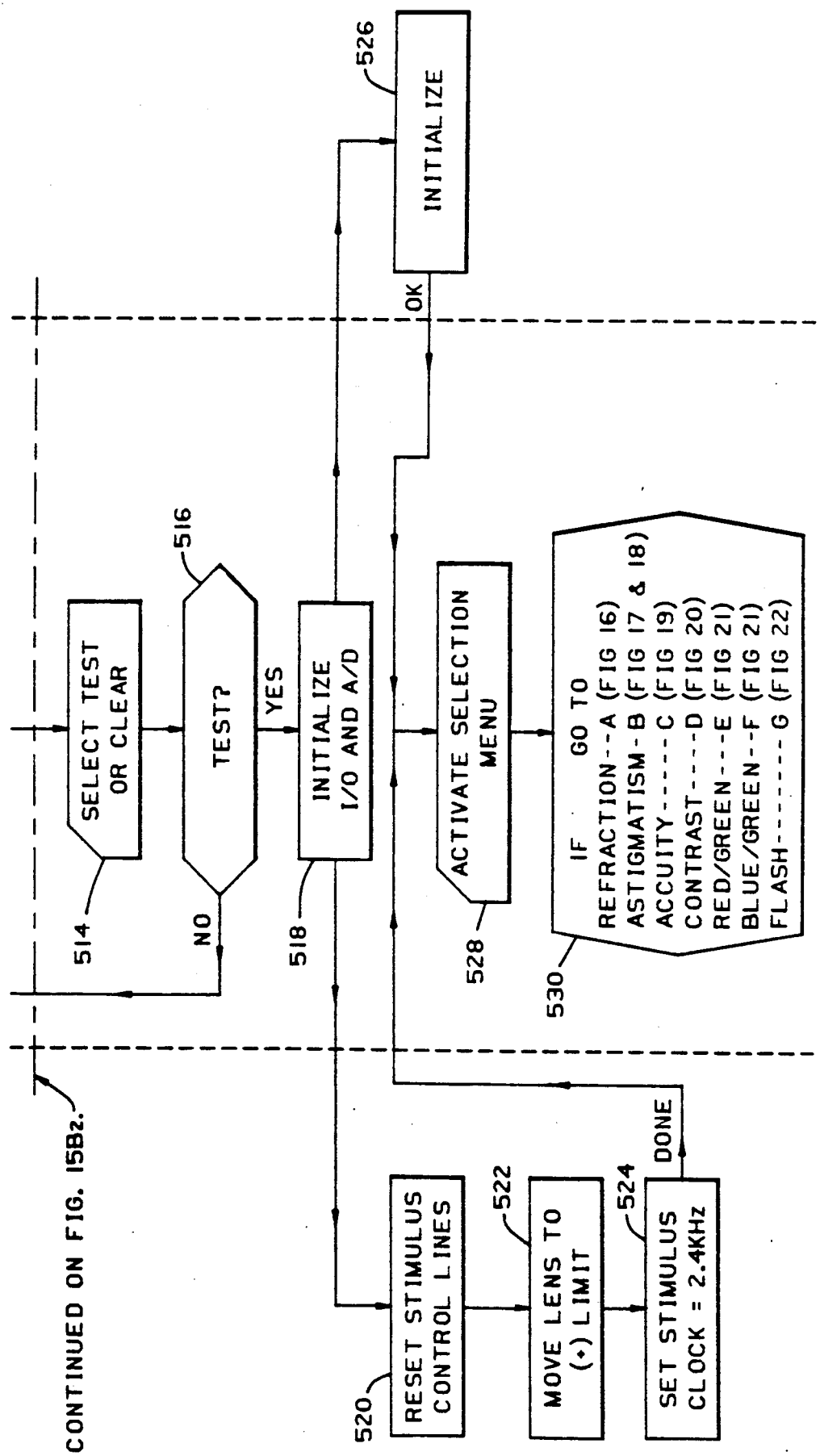

FIGS. 15A-15C illustrate the initialization and supervisor routines which allow entry of patient data, initialization of the control processor 12 and A-D converter 14 and selection of the appropriate test. This routine generally retrieves patient data, starts clocks, resets inputs and outputs and then branches to the selected test. At the beginning, the doctor or test technician inserts a patient record disk 502 and enters the patient's name 503. If the patient is a new patient, the patient's background is entered 506 and stored on the disk. If this is an old patient, then the old patient's history is displayed 512. If a test is to be conducted 516, the supervisor microcomputer 10 sends initialization commands to the control processor 12 and the analog to digital converter 14. The control processor 12 resets 520 the stimulus control lines and moves 522 the test lense to the positive limit by driving the stepper motor 4 for at least the range of movement of the lense. For example, if the lense can be moved from the positive to the negative limit in 500 steps, the control processor 12 initialization routine drives the lense at least 500 steps to ensure that the lense is at the positive limit. Once the lense is at the positive limit, the stimulus clock is started 524 followed by sending an initialization completed indicator or word to the supervisor computer 10. When both the test control processor 12 and programmable analog to digital converter 14 acknowledge that initialization is completed, a menu is displayed 528 which allows the operator to select among the various tests. The procedure than jumps 530 to the appropriate test of routine.

Figure 16A:
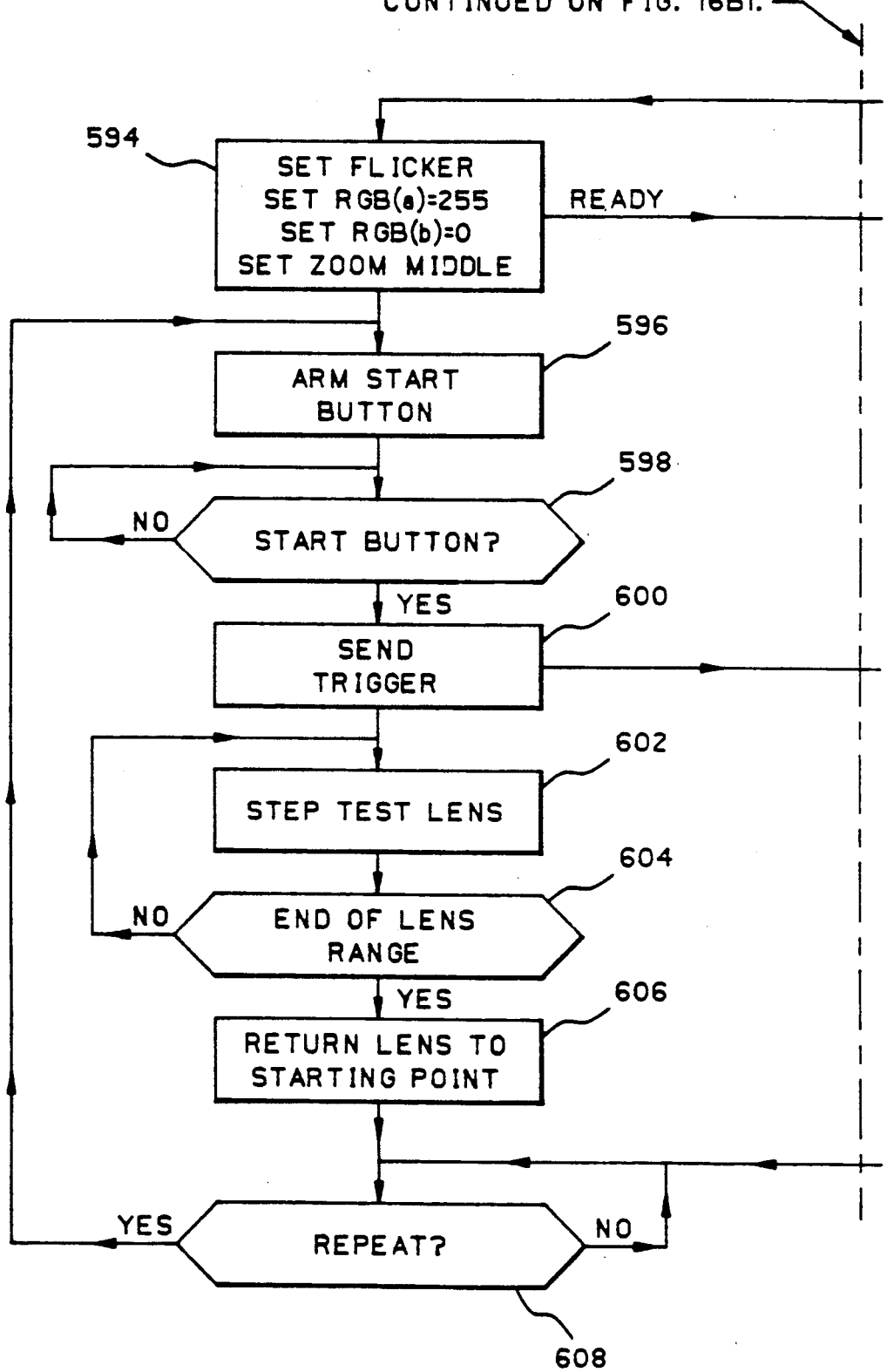

FIGS. 16A-16C illustrate the procedures performed by the control processor 12, supervisor microcomputer 10 and programmable analog to digital converter 14 when a spherical refractometry test is performed. Generally, this test sweeps the test lense 44 from one range limit to the other range limit of the test lense 44 and plots the amplitude of the steady state evoked potential. First, the supervisor microcomputer 10 sends 534 a command to the control processor 12 to begin the refraction test. When the control processor 12 is ready, it sends an acknowledgement to the supervisor microcomputer 10 which then sends 538 a command to the analog to digital converter 14 to digitize a test voltage. When the test voltage is digitized, it is displayed 544 as a bar graph and then the supervisor processor 10 waits 546 until it receives a trigger from the control processor 12 indicating that the test has started. When the test has started, the supervisor microcomputer 10 sends 548 a command to the analog to digital converter 14 to collect data points. When the data points have all been collected 550, the supervisor computer 10 performs 552 a low pass filter function on the data and displays 554 the data curve. The details of the low pass filter function can be found in U.S. application Ser. No. 727,032, mentioned in the Cross References to Related Applications section.

The technician or doctor can then examine the curve to determine whether a good vision test has been performed and choose whether 558 to save the data for averaging or discard this curve. If the data is to be saved for later averaging, it is stored 562 on the disk and a trial counter is incremented 564 and the test is repeated again. If the data is to be averaged, the average 572 is displayed 574 and the maximum is found 576. When the maximum is found, it is converted 578 into a diopter value which is then printed 580. The lense 44 position at which the maximum occurs, can be converted into lense diopter by using a conversion table. The supervisor computer 10 then displays 582 a menu which allows the average to be saved or the old average to be recalled and the test to be repeated. If the average is saved it is stored 588 on a disk and the menu is again displayed. If the old data is to be recalled, it is retrieved from the disk 592 and both the old and new data are both displayed 594.

The control processor 12 begins by setting 594 the flicker counters and moving the zoom lense to the middle by incrementing a down count line of the zoom control drive circuit for half the range. The control processor 12 then arms 596 a start button and awaits its activation 598. When the start button is depressed, the control processor 12 sends 600 the trigger indicating the start of the test to the supervisor 10. The control processor then steps 602 the lense 44 until the end of the range is reached 604 after which the lense 44 is returned 606 to the starting point. The control processor 12 then waits 608 for a signal to repeat the test.

Figure 18A:
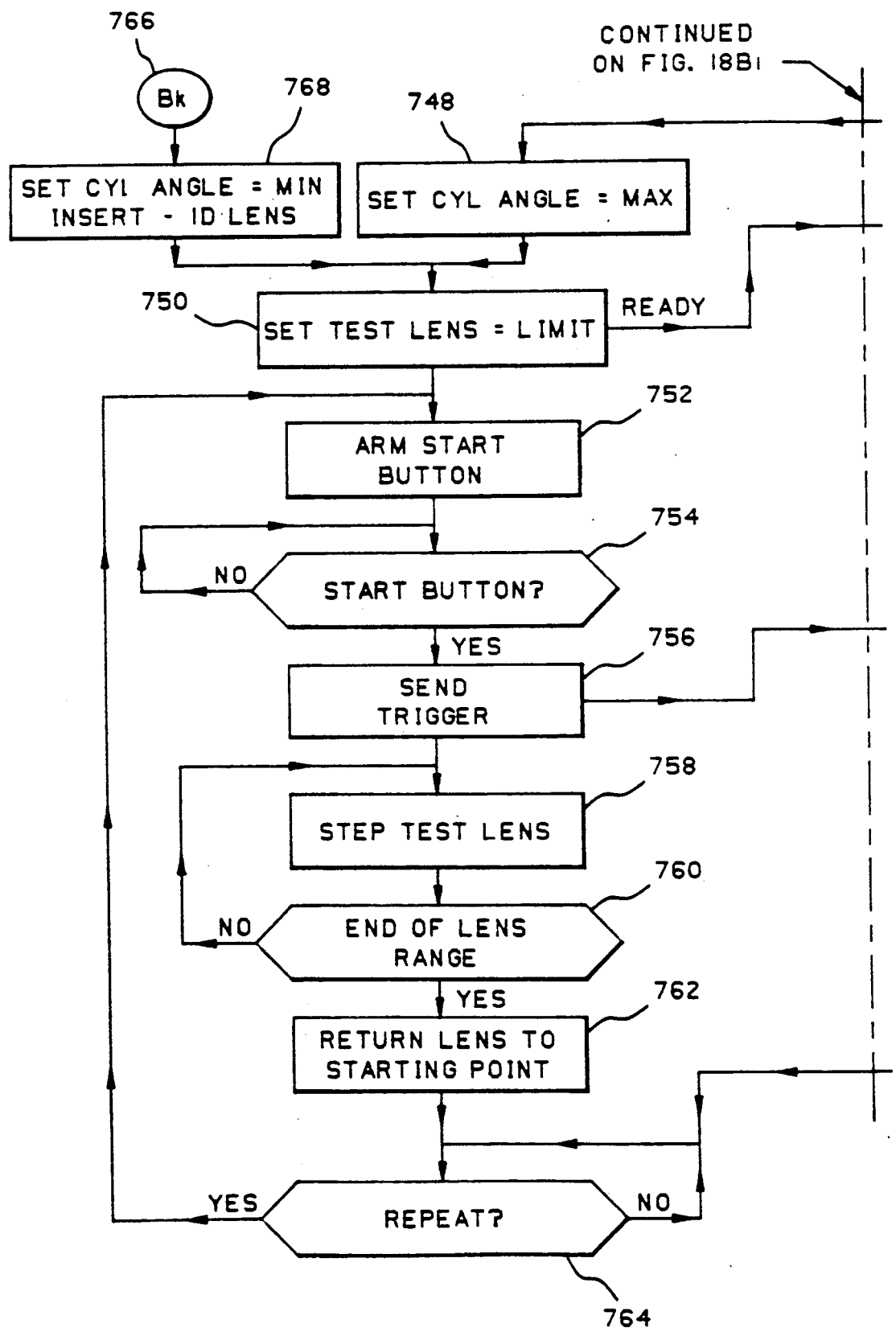

The astigmatism test is broken down into two parts, one for non-cylindrical power determination (FIG. 17A-17C) and one for cylindrical power determination (FIGS. 18A-18C). The astigmatism test is performed in substantially the same manner as the spherical refractometry test discussed immediately above and only those differences between the tests will be discussed below. In general, the cylindrical lense or slit is rotated at the refractive power diagnosed in the spherical test of FIGS. 16A-16C to determine the major and minor axes of vision. Once the axes are determined, two vision tests are conducted in which the test lense is swept through its range for each axis. In this test, 360 data points are taken in seven seconds, both the maximum and minimum of the refraction curve are found 656 and the maximum and minimum are converted 658 into an angle and the angle is printed 660 instead of the diopter. During set up, the control processor 12 sets 666 the zoom lense 36 to a middle value and the test lense 44 to the diagnosed diopter. In this test, the cylindrical lense 304 is stepped 674 until the end of this range 676 is reached (a 180 degree spin).

After the first part of the test is performed which determines the astigmatic axes without determining cylindrical power, the cylindrical power test of FIGS. 18A-18C are conducted. This test is performed in the same manner as the refractometry test of FIG. 16 except that the angle of the cylindrical lense 304 or slit 32 is first set 748 at the maximum angle to find the refracted power associated with the major axis. That is, during the first pass, the cylindrical lense 304 or slit 32 is set at the maximum angle. The test lense 44 is set at its positive limit 750 and the test lense 44 is stepped 758 through its range to determine diopter on the major axes. Then the cylindrical lense 304 or slit 32 is set 768 at its minimum angle followed by the insertion of a minus one diopter lense. The test lense 44 is then again stepped through the range to determine the diopter on the minor axis. In this way, two refractive curves are produced, one for each axis of an astigmatic eye.

Figure 19A:
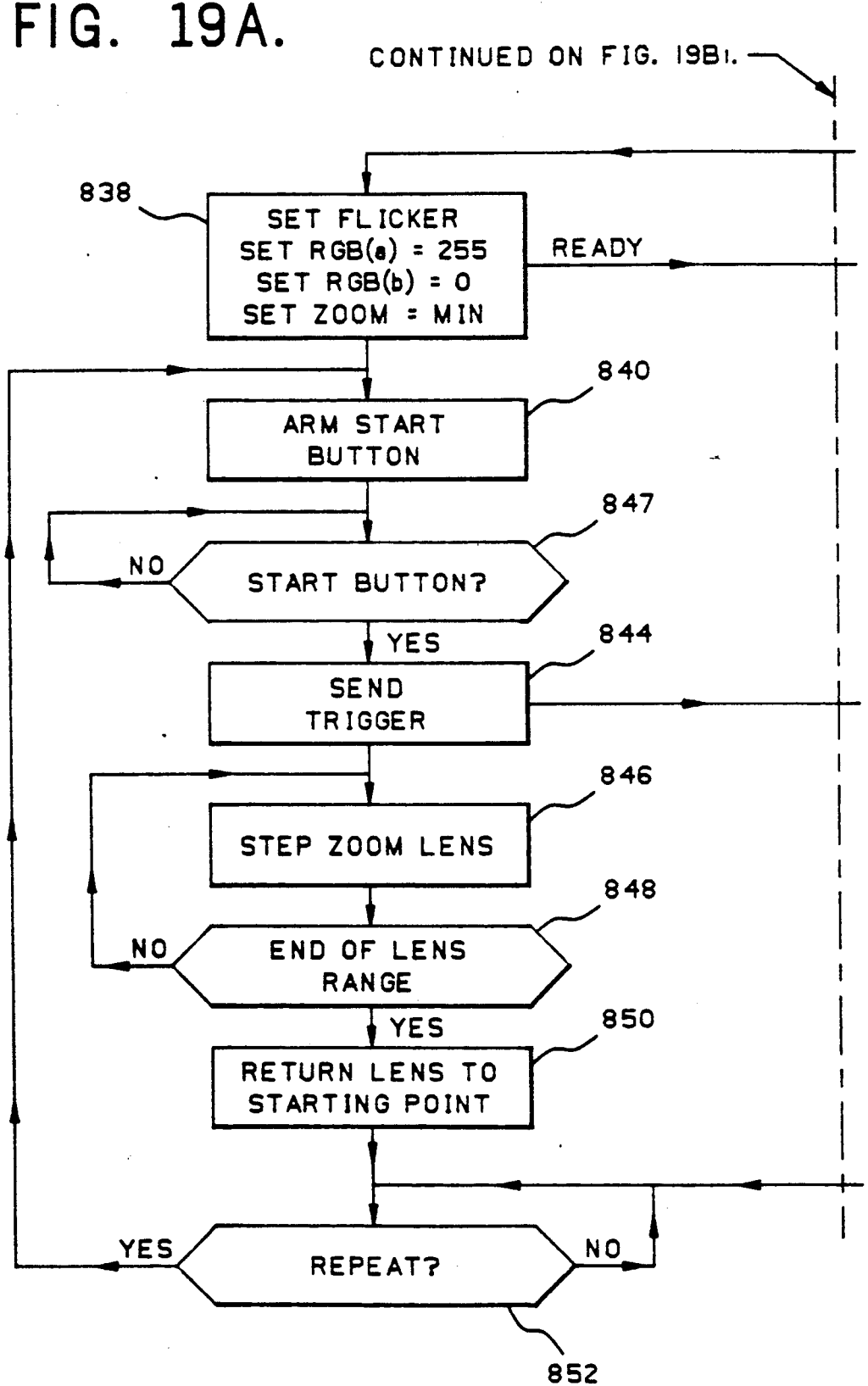

In the acuity test illustrated in FIGS. 19A-19C, the supervisor computer 10 performs a linear regression fit 814 to find the intercept of the diopter curve with the base line which is then displayed 816. The intercept is converted 820 into an acuity value which is then printed 822. In this test, the control processor steps 846 one of the zoom lenses 300 and 302 down from its maximum zoom value instead of the test lense or cylindrical lense. That is, the size of the pattern is changed as the zoom lense is stepped.

Figure 20A:
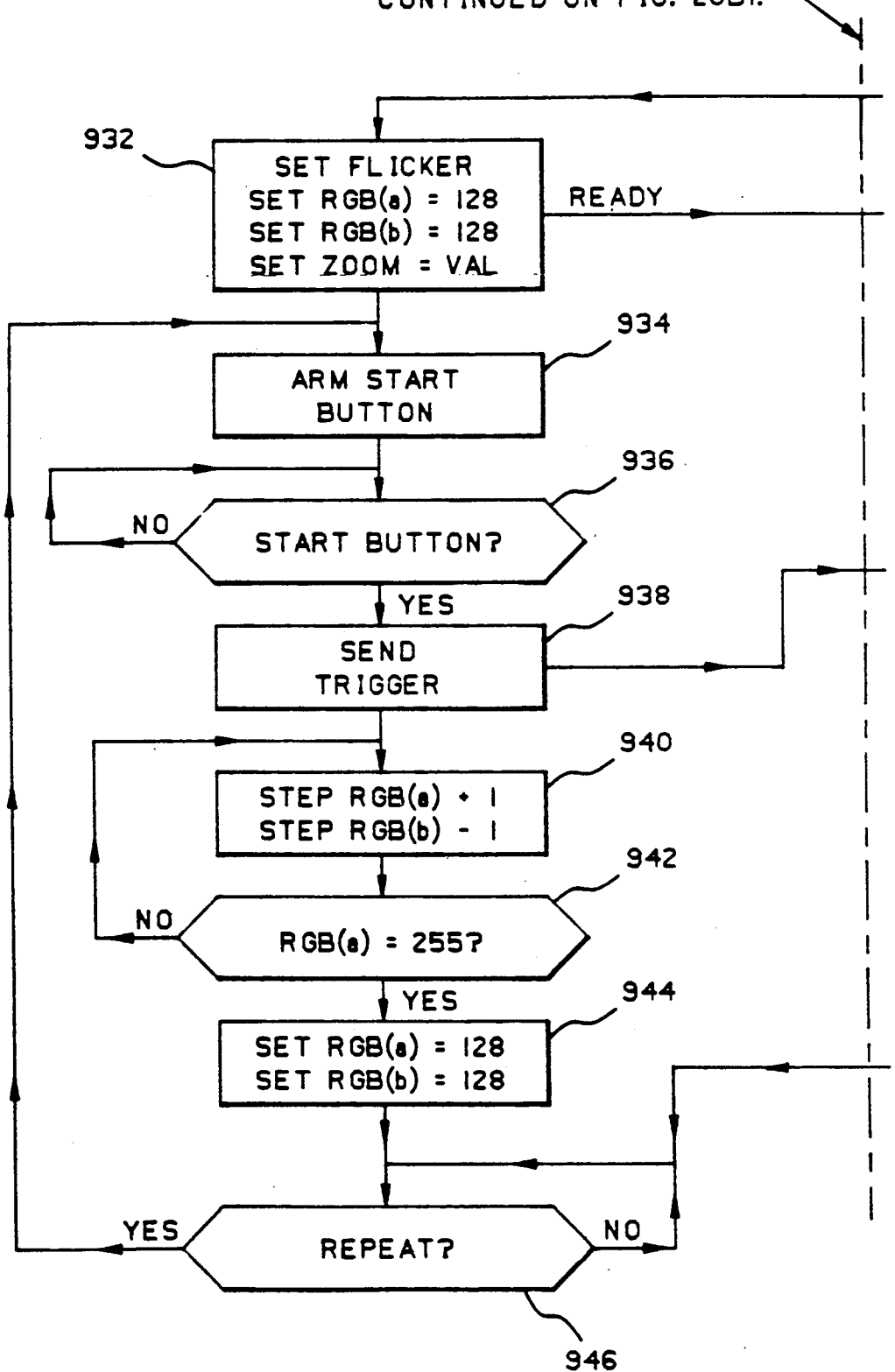
Figure 22A:
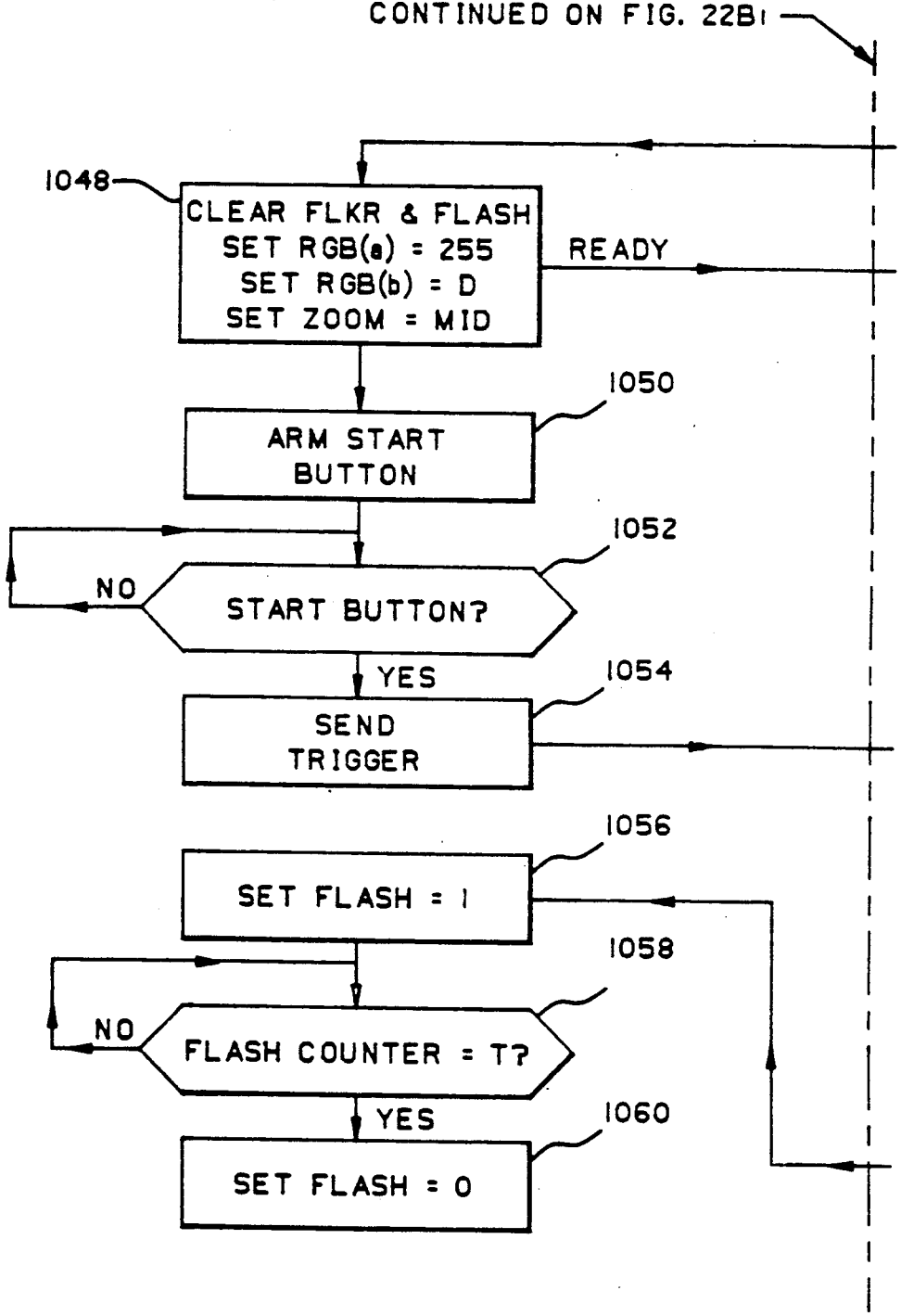

The procedure for the contrast sensitivity test is illustrated in FIGS. 20A-20C. In this test, a linear regression 900 is performed to determine and display 902 the intercept which is converted 906 into a contrast threshold which is printed The system then plots the threshold versus the spatial frequency. During this test, the stimulus control processor 12 sets 932 the zoom lense 300 or 302 at a desired value while the intensity of the opposite colors are changed 940 by stepping the color counter for the paths A/B and C. At the end of each detection, a new spatial frequency is selected 928, that is, a new value for the zoom lense is selected and the contrast sweep is performed again. When several threshold values are obtained, the spatial frequency versus threshold is plotted.

The color vision test procedure is illustrated by FIGS. 21A-21C. Once again, only those portions of the test which are different from previous tests will be discussed in detail. In this test, the average curves are displayed until a color vision dip is detected while the red and green or blue and green intensities are changed. The control processor 12 sets 1004 the zoom lense 300 or 302 to a middle value and steps 1012 the color control lines in opposite directions for red and green or blue and green so that the colors are swept through their ranges to allow detection of a dip in the evoked potential signal as illustrated in FIG. 14.

The flash test and transient pattern test are performed using the same procedure; however, the flash signal line is used to flash the wash source or tricolored sources in the flash test and used to trigger a pattern reversal in the transient pattern test. During the test, the amplifier 54 is connected directly to the A/D converter 14 which samples 1032 one thousand data points and the supervisor 10 displays 1044 the resulting curve. The control processor 12 initiates the flash or pattern reversal by setting 1056 a flash output line.

Figure 23:
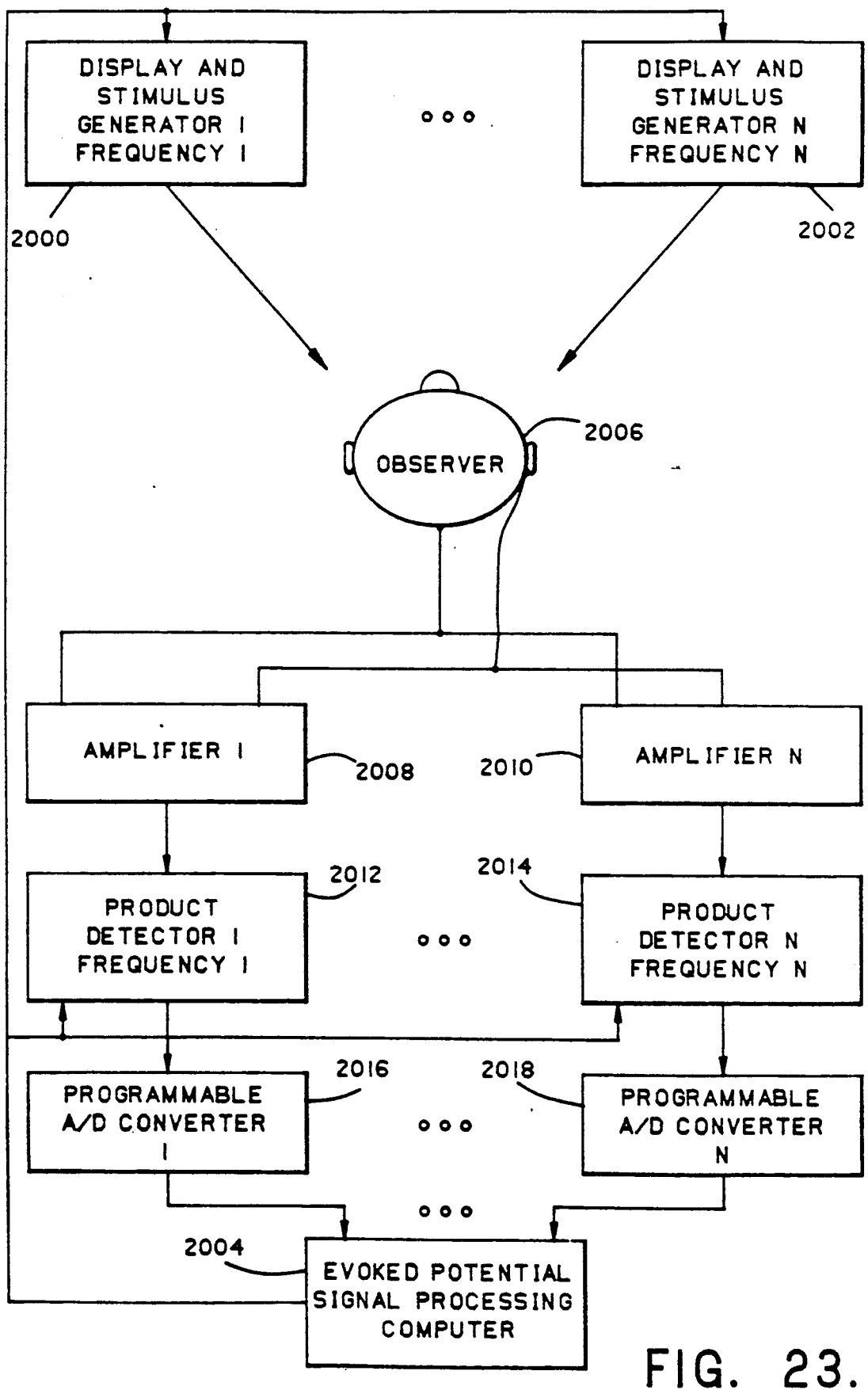
FIG. 23 depicts a system which will allow determination of which object an observer is viewing.

The components discussed herein can be combined to produce a system that can detect to which of several different displays an observer 2000 is paying attention. Such a system for monitoring visual attention is illustrated in FIG. 23. Combined display and stimulus generators 2000-2002 produce displays that either each blink at different frequencies as determined by control clocks from computer 2004 or each has a small portion that blinks at a different frequency. That is, display 2000 or a portion thereof blinks at a first frequency and display 2004 blinks at a different frequency Which preferably are a minimum of 0.1 to 0.5 Hz apart. The blink frequency should be above the flicker fusion frequency at which the observer 2004 can consciously detect the blinking. The flicker fusion frequency is approximately 15 Hz and the brain of a human observer will respond to blink frequencies as high as 180 Hz, even though the blinking is not consciously detectable. Each display 2000-2002 could be a combined optical system as depicted in FIG. 1 or could be a specially designed cathode ray tube (CRT) or vector scan CRT capable of blinking at specified frequencies or the displays could be combined onto a single display as long as the individual images to which the observer directs his attention blink at different frequencies.

The evoked potentials produced by the observer 2006 are amplified by narrow band amplifiers 2008-2010. It is also possible to substitute a single broad spectrum amplifier for the amplifier 2008-2010; however, some sacrifice in signal quality will have to be accepted. The amplified evoked potentials at each different blink frequency are detected by product detectors 2012-2014 using the same clock signals from the computer 2004 that drive generators 2000-2002. When the observer 2006 is paying attention to a particular display, the signal produced by the corresponding product detector in less than one second after attention is focused, will be much stronger than that from the other product detectors. A/D converters 2016-2018 convert the amplitude signals which are then compared by the evoked potential signal processing computer 2004 to determine which display 2000-2002 is getting the greatest attention.

This type of system is useful in measuring human attention to different displays or portions of a display (monitoring eye movement) in an advertising survey. It will also be useful in weapons fire control systems when cognitive controlled weapons become a reality. The system is further useful in alarm systems to determine whether the operator of a critical process is aware of and paying attention to a particular alarm, allowing the intensity of the alarm to be adjusted upward until the operator pays attention to the alarm.

The many features and advantages of the invention are apparent from the detailed specification and thus, it is intended by the appended claims to cover all such features and advantages of the invention which fall within the true spirit and scope thereof. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed is:

1. A product detector, comprising:

narrow band filter means for removing noise from evoked potentials produced by a patient at a predetermined frequency;

modulation means for detecting the evoked potentials at the predetermined frequency, said modulation means comprising a programmable gain control amplifier connected to said narrow band filter means; and demodulation means for producing an amplitude of the evoked potentials at the predetermined frequency.

* * * * *